US012702336B2

(12) United States Patent
Ihara et al.

(10) Patent No.: US 12,702,336 B2
(45) Date of Patent: Aug. 11, 2026

(54) PULSE MEASUREMENT DEVICE, BIOLOGICAL INFORMATION ESTIMATION DEVICE, PULSE MEASUREMENT METHOD, AND RECORDING MEDIUM

(71) Applicant: NEC Corporation, Tokyo (JP)

(72) Inventors: Kazuki Ihara, Tokyo (JP); Hiroyuki Endoh, Tokyo (JP)

(73) Assignee: NEC CORPORATION, Tokyo (JP)

( * ) Notice: Subject to any disclaimer, the term of this patent is extended or adjusted under 35 U.S.C. 154(b) by 232 days.

(21) Appl. No.: 18/688,832

(22) PCT Filed: Sep. 21, 2021

(86) PCT No.: PCT/JP2021/034502

§ 371 (c)(1),
(2) Date: Mar. 4, 2024

(87) PCT Pub. No.: WO2023/047445

PCT Pub. Date: Mar. 30, 2023

(65) Prior Publication Data

US 2024/0277273 A1 Aug. 22, 2024

(51) Int. Cl.
*A61B 5/16* (2006.01)
*A61B 5/00* (2006.01)
(Continued)

(52) U.S. Cl.
CPC .......... *A61B 5/165* (2013.01); *A61B 5/02427* (2013.01); *A61B 5/7267* (2013.01);
(Continued)

(58) Field of Classification Search
CPC ... A61B 5/165; A61B 5/02427; A61B 5/7267; A61B 5/743; A61B 5/02; A61B 5/02416;
(Continued)

(56) References Cited

U.S. PATENT DOCUMENTS

2002/0095077 A1* 7/2002 Swedlow ............. A61B 5/1495 600/323
2005/0149467 A1* 7/2005 Ono ........................ G06F 3/011 706/1
(Continued)

FOREIGN PATENT DOCUMENTS

JP 2016-154648 A 9/2016
JP 2016-537069 A 12/2016
(Continued)

OTHER PUBLICATIONS

JP Office Action for JP Application No. 2023-549179, mailed on Oct. 29, 2024 with English Translation.
(Continued)

*Primary Examiner* — Boniface N Nganga
(74) *Attorney, Agent, or Firm* — Sughrue Mion, PLLC

(57) ABSTRACT

A pulse measurement device including a plurality of light emitters which are disposed on a measurement surface of a substrate to be attached to the skin of a subject to be subjected to pulse measurement and emit light toward the skin of the subject, a light receiver which is disposed on the measurement surface of the substrate and comprises a plurality of light reception units that receive reflected light of the light emitted from the light emitters, and a control unit which causes the light emitters to emit light, receives, reception signals corresponding to the reflected light received by the light receiver from the light receiver, optimizes the intensity of the reception signals using a normalization constant set for the respective light emitters, and outputs the reception signals having intensities optimized using the normalization constants as a pulse signals.

11 Claims, 28 Drawing Sheets

(51) Int. Cl.
*A61B 5/024* (2006.01)
*G16H 20/70* (2018.01)

(52) U.S. Cl.
CPC ............. *A61B 5/743* (2013.01); *G16H 20/70* (2018.01); *A61B 2560/0223* (2013.01); *A61B 2560/0462* (2013.01); *A61B 2562/046* (2013.01)

(58) Field of Classification Search
CPC ... A61B 5/02438; A61B 5/681; A61B 5/0245; A61B 5/16; A61B 2560/0223
See application file for complete search history.

(56) References Cited

U.S. PATENT DOCUMENTS

2009/0326352 A1* 12/2009 Cheng .................... A61B 5/021
600/324
2016/0278646 A1* 9/2016 Hu ....................... A61B 5/7475
2017/0340257 A1* 11/2017 Aung ..................... A61B 5/024
2018/0132767 A1 5/2018 Rajan et al.
2020/0205677 A1* 7/2020 Ito ........................ A61B 5/7257

FOREIGN PATENT DOCUMENTS

JP 2018-504188 A 2/2018
JP 2018-029870 A 3/2018
WO 2021/009851 A1 1/2021

OTHER PUBLICATIONS

International Search Report for PCT Application No. PCT/JP2021/034502, mailed on Nov. 9, 2021.
English translation of Written opinion for PCT Application No. PCT/JP2021/034502, mailed on Nov. 9, 2021.
Yokota, et al., "A conformable imager for biometric authentication and vital sign measurement", Nature Electronics, vol. 3, pp. 113-121 (2020).

* cited by examiner

Fig.1

10
14
17
11
120
120
120
11
17
(E1)
(R1)
(R2)
(R3)
(E2)
SKIN
BLOOD VESSEL

Fig. 14

190
194
197
192
193
191
192
197
SKIN
BLOOD VESSEL

Fig.17

INTENSITY

TIME

INTENSITY

TIME

Fig. 18

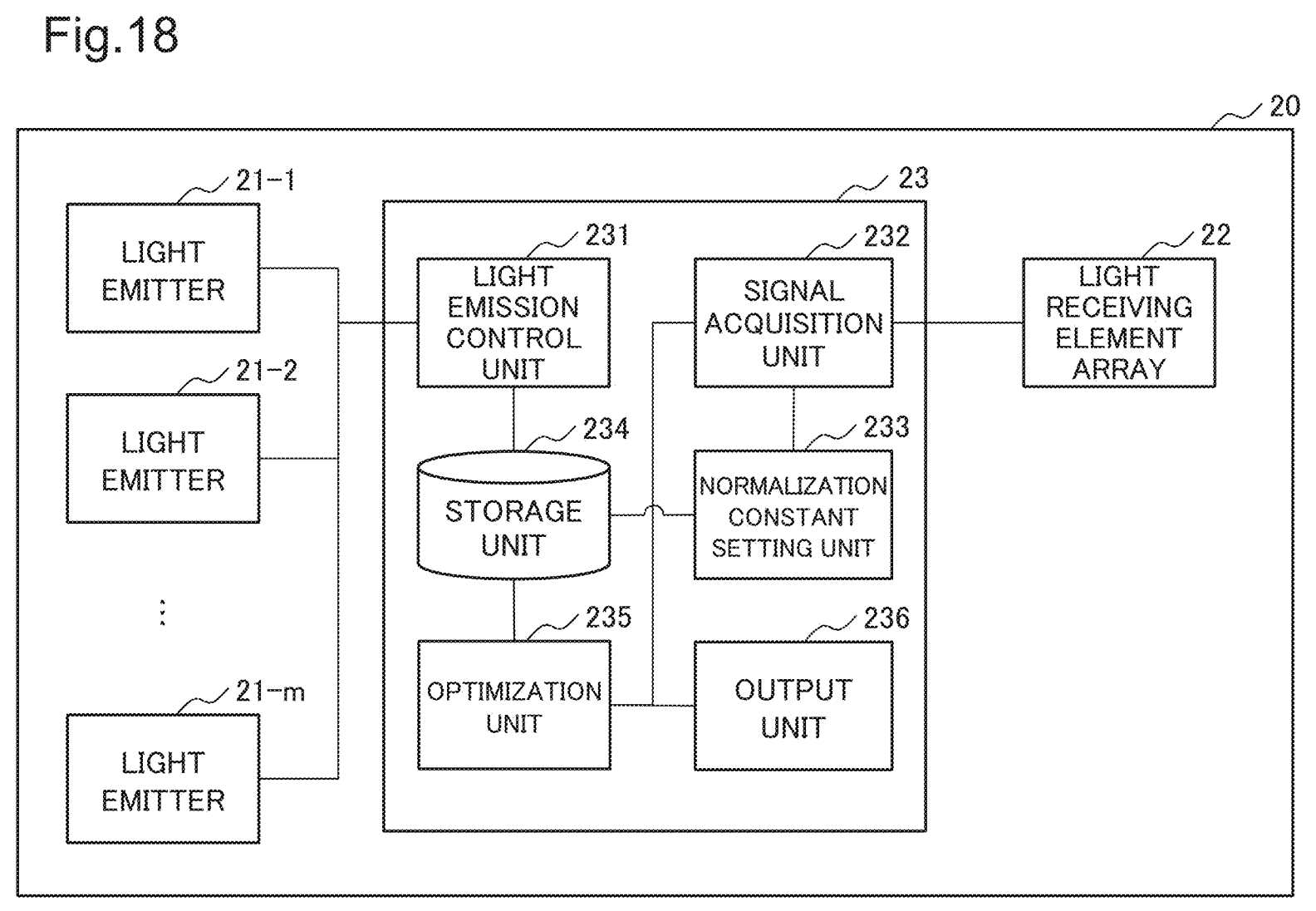

20
22 LIGHT RECEIVING ELEMENT ARRAY
23
232 SIGNAL ACQUISITION UNIT
233 NORMALIZATION CONSTANT SETTING UNIT
236 OUTPUT UNIT
231 LIGHT EMISSION CONTROL UNIT
234 STORAGE UNIT
235 OPTIMIZATION UNIT
21-1 LIGHT EMITTER
21-2 LIGHT EMITTER
...
21-m LIGHT EMITTER

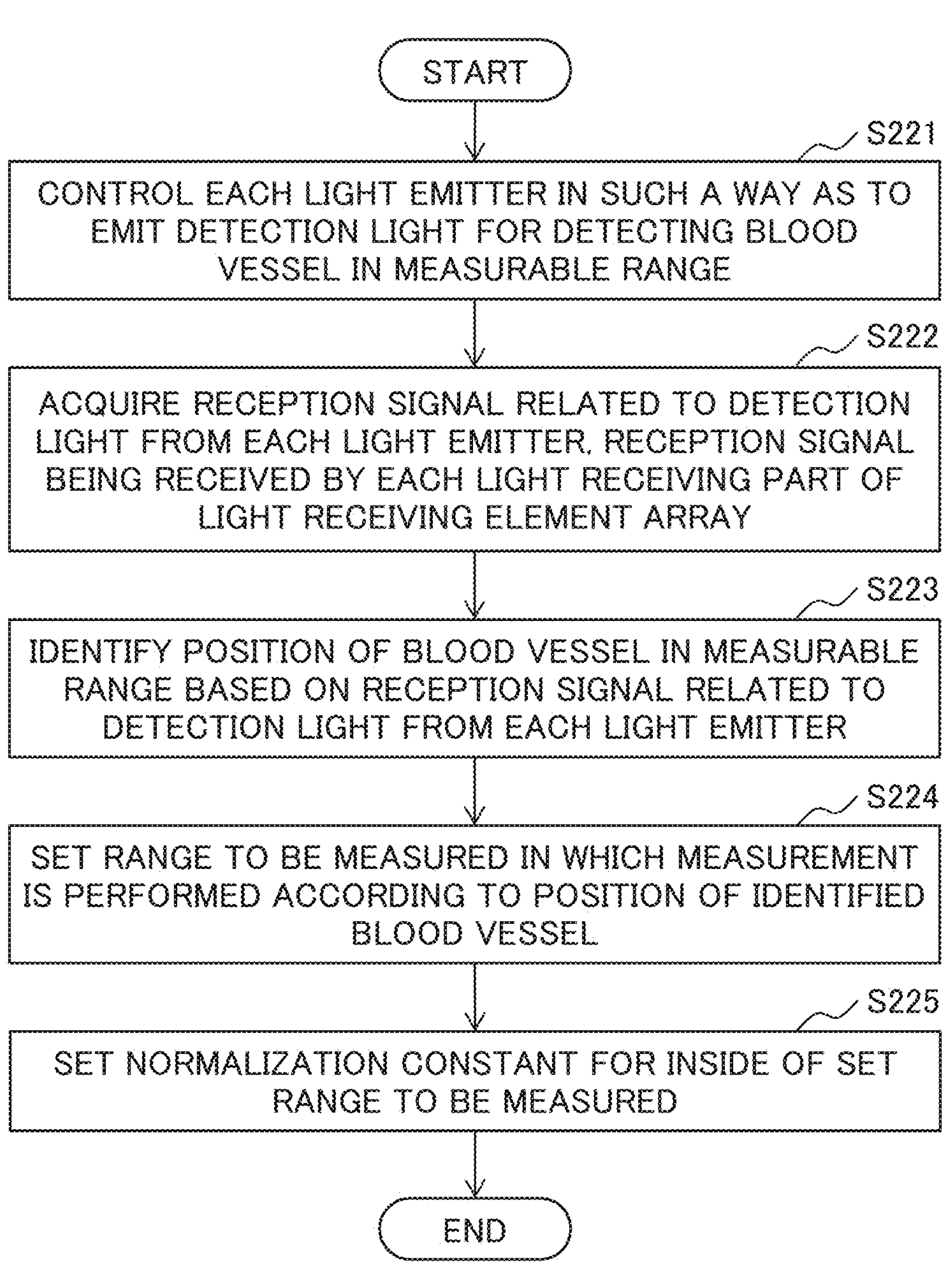
Fig.26
START
S221
CONTROL EACH LIGHT EMITTER IN SUCH A WAY AS TO EMIT DETECTION LIGHT FOR DETECTING BLOOD VESSEL IN MEASURABLE RANGE
S222
ACQUIRE RECEPTION SIGNAL RELATED TO DETECTION LIGHT FROM EACH LIGHT EMITTER, RECEPTION SIGNAL BEING RECEIVED BY EACH LIGHT RECEIVING PART OF LIGHT RECEIVING ELEMENT ARRAY
S223
IDENTIFY POSITION OF BLOOD VESSEL IN MEASURABLE RANGE BASED ON RECEPTION SIGNAL RELATED TO DETECTION LIGHT FROM EACH LIGHT EMITTER
S224
SET RANGE TO BE MEASURED IN WHICH MEASUREMENT IS PERFORMED ACCORDING TO POSITION OF IDENTIFIED BLOOD VESSEL
S225
SET NORMALIZATION CONSTANT FOR INSIDE OF SET RANGE TO BE MEASURED
END

300

EMOTION ESTIMATION RESULT "ANGER"

36

BIOLOGICAL INFORMATION PROCESSING DEVICE

LET'S CONSIDER CALMING DOWN SO THAT YOU FEEL RELAXED.

91 PROCESSOR

92 MAIN STORAGE DEVICE

93 AUXILIARY STORAGE DEVICE

98

95 INPUT / OUTPUT I/F

96 COMMUNICATION I/F

NETWORK

PULSE MEASUREMENT DEVICE, BIOLOGICAL INFORMATION ESTIMATION DEVICE, PULSE MEASUREMENT METHOD, AND RECORDING MEDIUM

This application is a National Stage Entry of PCT/JP2021/034502 filed on Sep. 21, 2021, the contents of all of which are incorporated herein by reference, in their entirety.

TECHNICAL FIELD

The present disclosure relates to a pulse measurement device or the like that measures a pulse.

BACKGROUND ART

There is a technique of detecting biological information reflecting an activity of an autonomic nerve system such as a variation in pulse from a subject and estimating an emotion of the subject according to the detected biological information. PTL 1 discloses a method for deriving a mental state of a subject using a bio signal detected for the subject. In PTL 1, a statistical variation is calculated with respect to a plurality of physiological parameters derived from a bio signal, and an excitement level of a subject is determined based on the calculated statistical variation. In PTL 1, a time domain heart rate variability signal is derived from a bio signal to calculate a plurality of heart rate variability parameters, and an emotional valence level of a subject is determined based on calculated values of the plurality of heart rate variability parameters. In the method of PTL 1, a mental state of a subject is derived according to an excitement level and an emotional valence level.

NPL 1 discloses a flexible imaging device in which a high-resolution array-shaped sensor is mounted on a flexible substrate. The device of NPL 1 has a structure in which a polysilicon thin-film transistor readout circuit and an organic photodiode having high sensitivity in a near-infrared region are combined. The device of NPL 1 can acquire biological information such as a pulse or a vein image of a subject with high resolution by being attached to the skin of the subject.

CITATION LIST

Patent Literature

PTL 1 JP 2018-504188 A

Non Patent Literature

NPL 1: T. Yokota, et al., "A conformable imager for biometric authentication and vital sign measurement", Nature Electronics, volume 3, p.p. 113-121 (2020).

SUMMARY OF INVENTION

Technical Problem

By using biological information measured by the device of NPL 1, the mental state of the subject can be derived by the method of PTL 1. In order to accurately estimate the mental state of a subject, it is necessary to accurately measure biological information of the subject. In the method of NPL 1, the measurement condition of the pulse signal to be detected is non-uniform in the plane of the array-shaped sensor due to the influence of the environment under the skin to which the device is attached, the difference in the distance between the light source and the sensor, and the like. In the method of NPL 1, it is difficult to make the measurement condition of the pulse signal uniform in the plane of the array-shaped sensor because it is affected by artifacts caused by the heartbeat and the body motion. That is, it is difficult to accurately measure the pulse of the subject by the method of NPL 1.

An object of the present disclosure is to provide a pulse measurement device or the like capable of accurately measuring a pulse of a subject.

Solution to Problem

A pulse measurement device according to an aspect of the present disclosure includes a plurality of light emitters that is disposed on a measurement face of a substrate to be attached to a skin of a subject to be subjected to pulse measurement and emits light toward the skin of the subject, a light receiver that is disposed on the measurement face of the substrate and includes a plurality of light receiving parts that receives reflected light of the light emitted from the plurality of light emitters, and a control unit that causes the plurality of light emitters to emit the light, receives, from the light receiver, a reception signal related to the reflected light of the light received by each of the light receivers, optimizes intensity of the reception signal using a normalization constant set for each of the plurality of light emitters, and outputs the reception signal having intensity optimized using the normalization constants as a pulse signal.

In a pulse measurement method according to an aspect of the present example embodiment using a plurality of light emitters that emits light toward a skin of a subject to be subjected to pulse measurement and a light receiver including a plurality of light receiving parts that receives reflected light of the light emitted from the plurality of light emitters, the pulse measurement method includes a control unit causing the plurality of light emitters to emit the light, receiving, from the light receiver, a reception signal related to the reflected light of the light received by each of the light receivers, optimizing intensity of the reception signal using a normalization constant set for each of the plurality of light emitters, and outputting the reception signal having intensity optimized using the normalization constants as a pulse signal.

In a program according to an aspect of the present example embodiment for controlling a plurality of light emitters that emits light toward a skin of a subject to be subjected to pulse measurement and a light receiver including a plurality of light receiving parts that receives reflected light of the light emitted from the plurality of light emitters, the program causes a computer to execute the steps of causing the plurality of light emitters to emit the light, receiving, from the light receiver, a reception signal related to the reflected light of the light received by each of the light receivers, optimizing intensity of the reception signal using a normalization constant set for each of the plurality of light emitters, and outputting the reception signal having intensity optimized using the normalization constants as a pulse signal.

Advantageous Effects of Invention

According to the present disclosure, it is possible to provide a pulse measurement device or the like capable of accurately measuring a pulse of a subject.

BRIEF DESCRIPTION OF DRAWINGS

FIG. 1 is a block diagram illustrating an example of a configuration of a pulse measurement device according to a first example embodiment.

FIG. 14 is a conceptual diagram illustrating an example of a configuration of a pulse measurement device according to a related art.

FIG. 17 is a conceptual diagram illustrating still another example of the signal measured by the pulse measurement device according to the related art.

FIG. 18 is a block diagram illustrating an example of a configuration of a pulse measurement device according to a second example embodiment.

FIG. 26 is a flowchart for describing an example of setting of a range to be measured by the pulse measurement device according to the second example embodiment.

FIG. 35 is a block diagram illustrating an example of a hardware configuration for implementing control and processing in each example embodiment.

EXAMPLE EMBODIMENT

Figure 2:
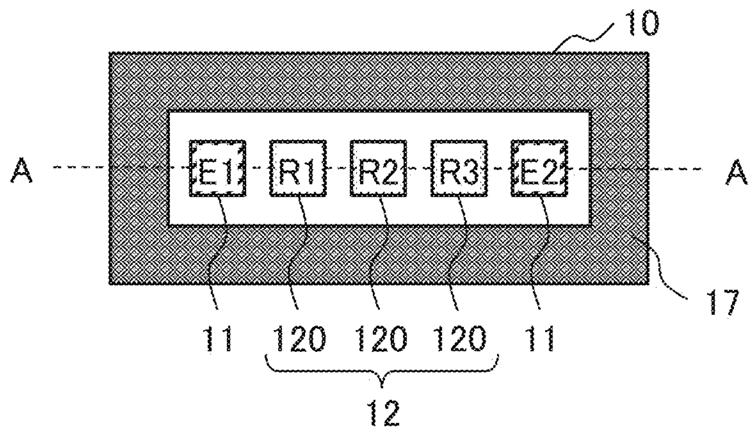
FIG. 2 is a conceptual diagram of the pulse measurement device according to the first example embodiment viewed from a measurement face side.

Hereinafter, embodiments of the present invention will be described with reference to the drawings. However, the example embodiments described below have technically preferable limitations for carrying out the present invention, but the scope of the present invention is not limited to the following. In all the drawings used in the following description of the example embodiment, the same reference numerals are given to the same parts unless there is a particular reason. In the following example embodiments, repeated description of similar configurations and operations may be omitted.

First Example Embodiment

First, a pulse measurement device according to a first example embodiment will be described with reference to the drawings. The pulse measurement device of the present example embodiment is attached to the skin of the subject. The pulse measurement device of the present example embodiment emits light from above the skin of the subject and receives reflected light of the light. The pulse measurement device of the present example embodiment measures the pulse of the subject according to the intensity change of the received reflected light.

(Configuration)

Figure 1:
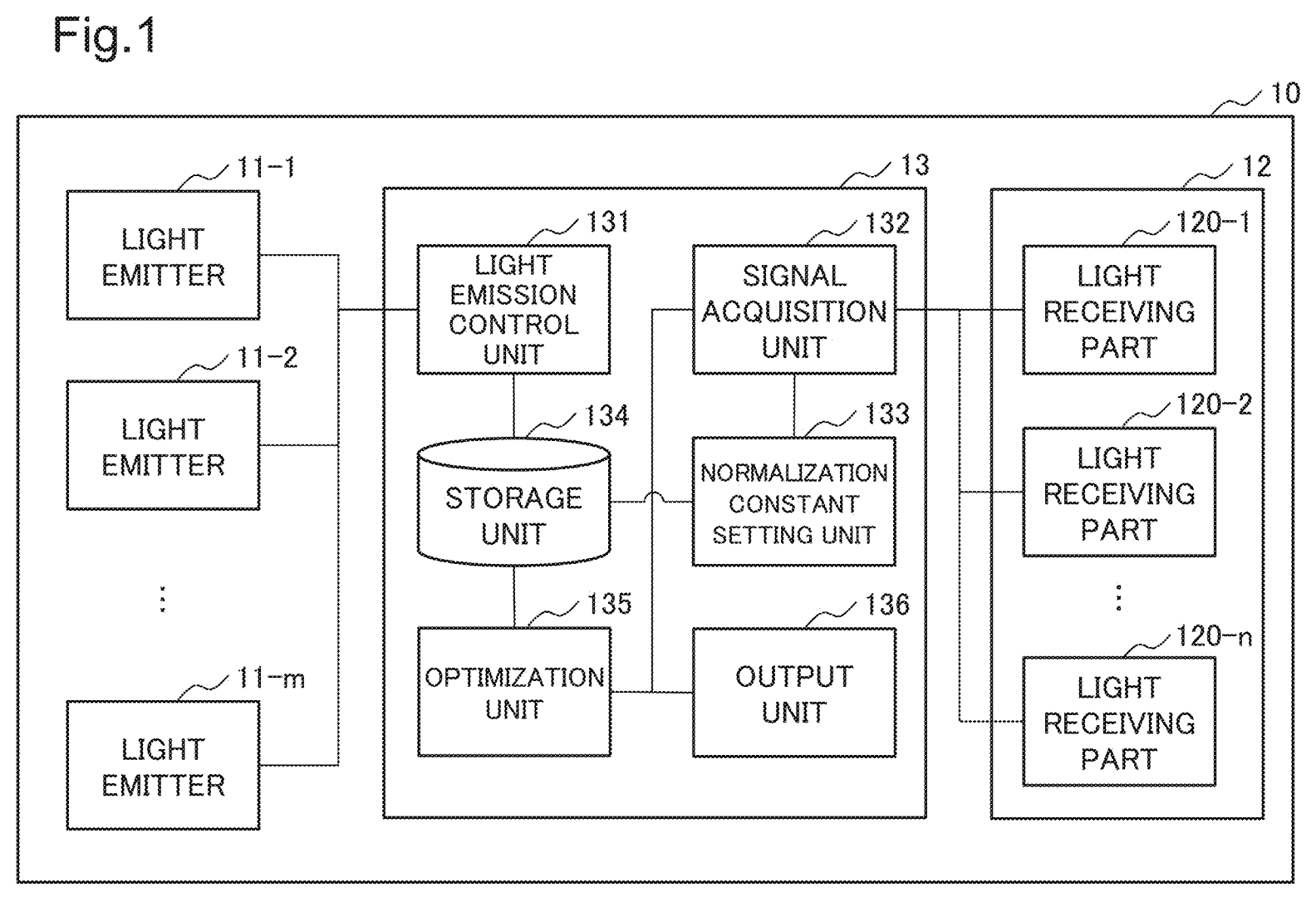

FIG. 1 is a block diagram illustrating an example of a configuration of a pulse measurement device 10 according to the present example embodiment. The pulse measurement device 10 includes a plurality of light emitters 11-1 to m, a light receiver 12, and a control unit 13 (m is a natural number equal to or more than 2). A light receiver 12 includes a plurality of light receiving parts 120-1 to n (n is a natural number equal to or more than 2). The control unit 13 includes a light emission control unit 131, a signal acquisition unit 132, a normalization constant setting unit 133, a storage unit 134, an optimization unit 135, and an output unit 136. Hereinafter, in a case where a matter common to the plurality of light emitters 11-1 to m is described, they may be referred to as a light emitter 11. Similarly, in the following description, in a case where matters common to the plurality of light receiving parts 120-1 to n are described, they may be referred to as a light receiving part 120.

Figure 3:
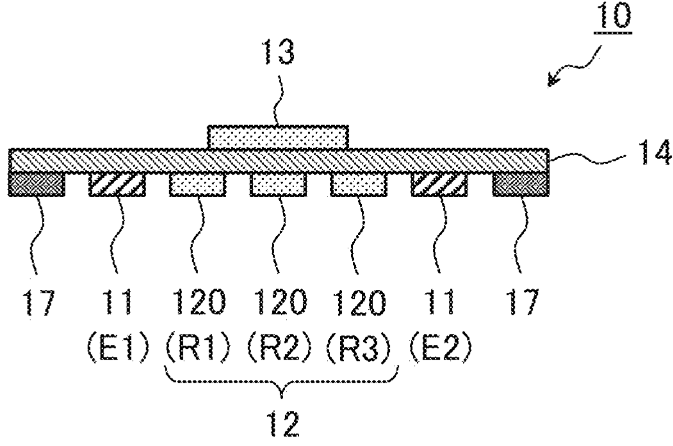
FIG. 3 is a cross-sectional view for describing a configuration of the pulse measurement device according to the first example embodiment.

FIG. 2 is a conceptual diagram of a measurement face of the pulse measurement device 10. FIG. 3 is a cross-sectional view of the pulse measurement device 10 taken along line A-A in FIG. 2. Hereinafter, an example in which the pulse measurement device 10 includes two light emitters 11 (E1, E2) and three light receiving parts 120 (R1, R2, R3) will be described. FIGS. 2 and 3 illustrate an example in which two light emitters 11 and three light receiving parts 120 are disposed on the same surface (also referred to as a measurement face) of a substrate 14. An adhesive layer 17 for attaching the pulse measurement device 10 to the skin of the subject is installed in a peripheral portion in the measurement face of the substrate 14. The pulse measurement device 10 is attached to the skin of the subject in such a way that light from the outside does not enter the measurement face side of the substrate 14 in a state of being attached to the skin. FIG. 3 illustrates an example in which the control unit 13 is disposed on a face facing the measurement face. The position where the control unit 13 is disposed is not limited to the face facing the measurement face. For example, the control unit 13 may be disposed inside the substrate 14 or at a position away from the light emitter 11 and the light receiver 12.

The light emitter 11 has an emission face that emits light used for measuring pulse. The light emitted from the light emitter 11 at the time of pulse measurement is also referred to as an optical signal. The plurality of light emitters 11 is disposed in such a way that their emission faces face the same direction. The emission faces of the plurality of light emitters 11 and the light receiving faces of the plurality of light receiving parts 120 are disposed in the same direction. The emission face of the light emitter 11 is directed to the skin of the subject in a state where the pulse measurement device 10 is attached to the skin of the subject.

The light emitter 11 emits an optical signal in a wavelength band capable of measuring a pulse. For example, the light emitter 11 is achieved by a light-emitting diode (LED). For example, the light emitter 11 emits an optical signal in a green wavelength band. For pulse measurement, an optical signal in a green wavelength band is preferable. For example, the light emitter 11 emits an optical signal in a near-infrared wavelength band. In the case of measuring the entire vein, for example, near infrared rays of about 1.1 micrometers are suitable. The wavelength band of the optical signal emitted from the light emitter 11 is not particularly limited as long as it is a wavelength band in which the pulse can be measured. The optical outputs of the plurality of light emitters 11 may be the same or different. The optical output of the plurality of light emitters 11 may be constant or adjustable. When the optical outputs of the plurality of light emitters 11 are adjustable, the optical output can be adjusted for each light emitter 11.

The light receiving part 120 includes a light receiving part that receives reflected light of the optical signal emitted from the light emitter 11. The reflected light is a light component that is reflected/scattered under the skin (inside the body) of the subject and reaches the light receiving part 120 in the optical signal emitted from the light emitter 11. For example, the light receiving part 120 is achieved by a photodiode sensitive to a wavelength band of an optical signal emitted from the light emitter 11.

The control unit 13 controls the plurality of light emitters 11. For example, the control unit 13 is achieved by a microcomputer (referred to as a maicon) or a microcontroller. For example, the control unit 113 includes a central processing unit (CPU), a random access memory (RAM), a read only memory (ROM), a flash memory, and the like. The control unit 13 executes control and processing according to a program stored in advance. The control unit 13 executes control and processing according to the program in accordance with a preset schedule, an instruction from the outside, or the like. For example, the control unit 113 stores the reception signal acquired from the light receiving part 120 in the flash memory. For example, the control unit 13 outputs the digital data stored in the flash memory at a predetermined timing.

Figure 4:
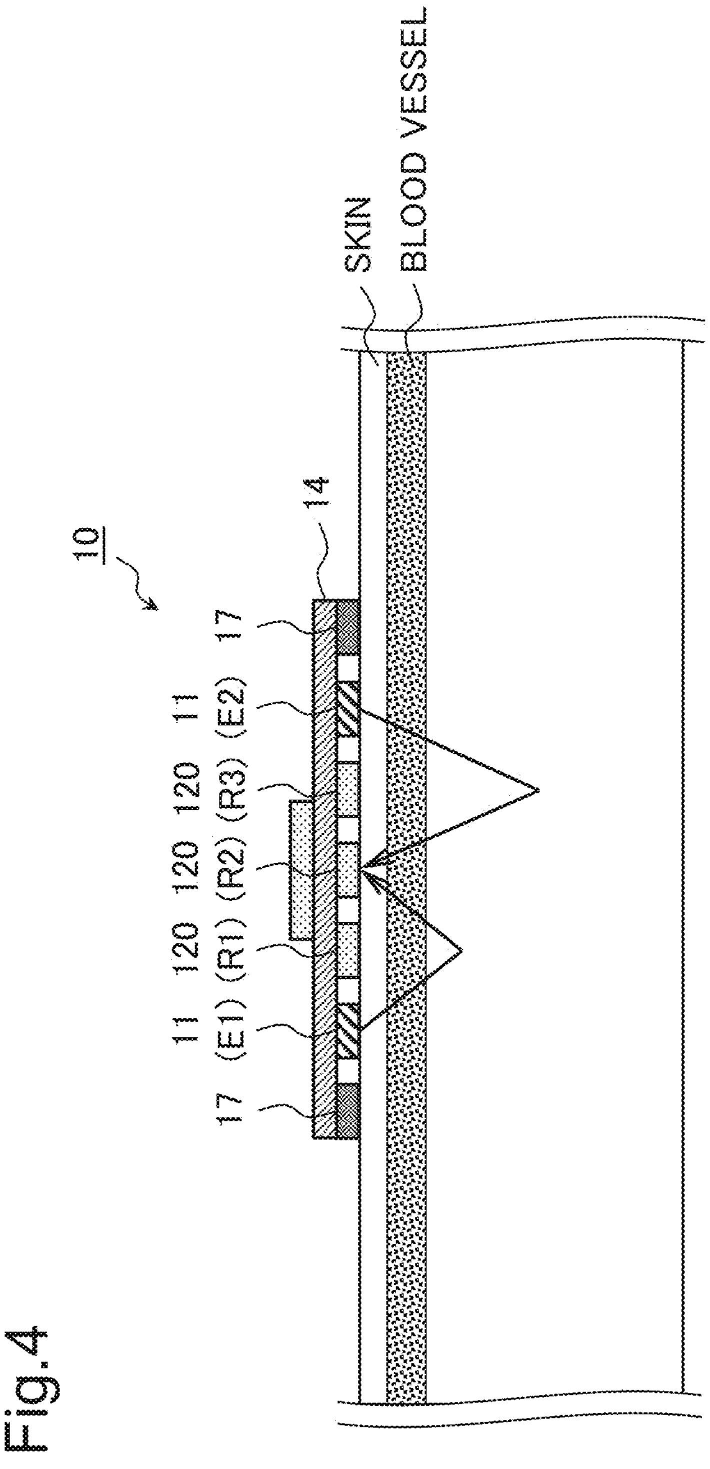
FIG. 4 is a conceptual diagram illustrating an example in which the pulse measurement device according to the first example embodiment is attached to the skin of a subject.

FIG. 4 is a conceptual diagram illustrating a state in which the optical signal emitted from the light emitter 11 is reflected/scattered under the skin (in the body) of the subject. The reflected light of the optical signal emitted from each of the plurality of light emitters 11 is received by each of the plurality of light receiving parts 120 via different paths. The light intensity of the optical signal emitted from each of the plurality of light emitters 11 changes according to light absorption characteristics and scattering characteristics by body constituent tissues such as skin, blood vessels, muscles, fat, and bone. Therefore, the light intensity of the reflected light received by the light receiving part 120 varies according to the length of the optical signal/reflected light path, the environment under the skin, and the body motion of the subject. In the present example embodiment, an optical signal is emitted from the light emitter 11 from above the skin of the subject toward the inside of the body, and the pulse of the subject is measured according to reflected light of the optical signal. For example, in the present example embodiment, a variation in the blood volume in the body due to pulsation is measured as a change in absorbance (also referred to as a light intensity change).

Figure 5:
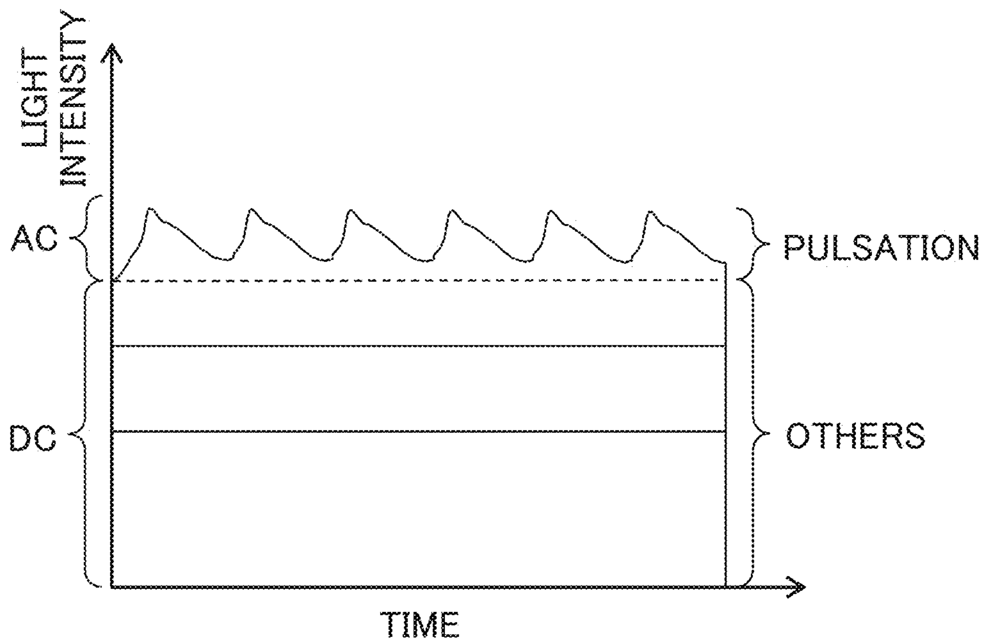
FIG. 5 is a conceptual diagram for describing a factor that affects light intensity of reflected light measured by the pulse measurement device according to the first example embodiment.

FIG. 5 is a conceptual diagram for describing factors that affect the light intensity of the reflected light received by the light receiving part 120. Factors that affect the light intensity of the reflected light include a fluctuation component and a stationary component. The fluctuation component is also referred to as an alternating current (AC) component. The AC component fluctuates due to pulsation. The stationary component is also referred to as a direct current (DC) component. The DC component hardly fluctuates due to pulsation. The pulse is measured based on the light intensity change of the reflected light according to the fluctuation of the AC component. In the present example embodiment, the fluctuation of the AC component is measured as pulsation.

Figure 6:
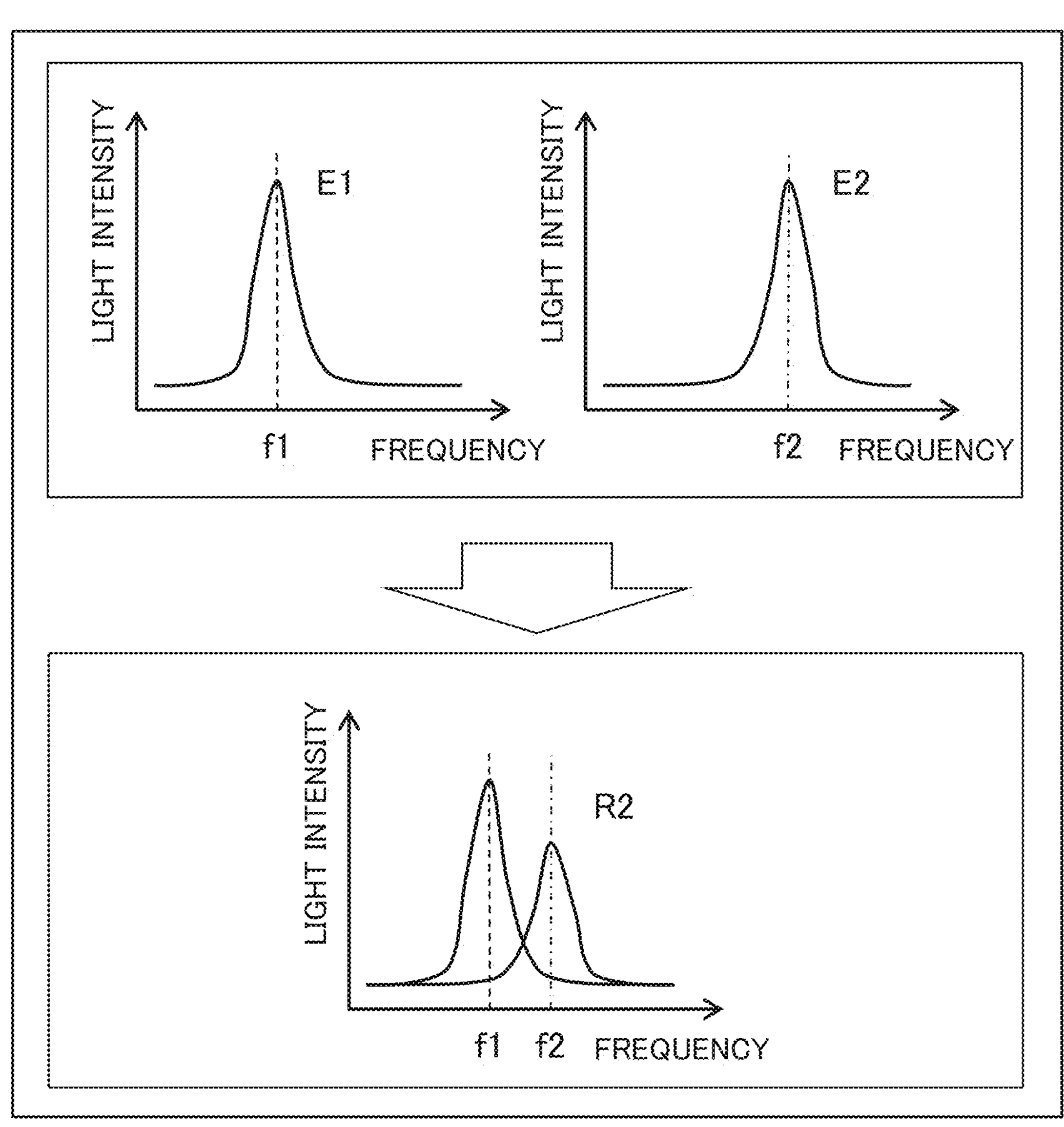
FIG. 6 is a conceptual diagram for describing an example of intensity of a reception signal related to reflected light measured by the pulse measurement device according to the first example embodiment.

FIG. 6 is a conceptual diagram for describing the light intensity of the reflected light in a case where the optical signals emitted from the plurality of light emitters 11 are received by the same light receiving part 120. The upper part of FIG. 6 (the upper side of the arrow) illustrates a waveform at the time of emission of the optical signal emitted by the light emitter 11 (E1, E2). The lower part of FIG. 6 (the lower side of the arrow) illustrates a waveform at the time of receiving the reflected light received by the light receiving part 120 (R2). In the example of FIG. 6, the light emitter E1 and the light emitter E2 emit optical signals having the same light intensity and different frequencies at the same timing. The light emitter E1 emits an optical signal having a frequency f1. The light emitter E2 emits an optical signal having a frequency f2. The light receiving part R2 receives reflected light of the optical signals emitted from the light emitter E1 and the light emitter E2 at the same timing. However, it is assumed that the difference in the light reception timing of the reflected light due to the difference between the distance between the light emitter E1 and the light receiving part R2 and the distance between the light emitter E2 and the light receiving part R2 is equal to or less than the detection limit. The reflected light of the optical signal emitted from the light emitter E1 and the reflected light of the optical signal emitted from the light emitter E2 are measured at different light intensity in the light receiving part R2 due to the influence of the distance of the path of the optical signal/reflected light, the environment under the skin, the body motion, and the like. In the present example embodiment, the waveform of the reflected light is optimized in such a way that the degree of influence of each of the plurality of light emitters 11 on each of the plurality of light receiving parts 120 is uniform.

An example of normalizing the reflected light received by the light receiving part 120 will be described. The degree of influence of the light emitter e on the light receiving part r is expressed as I(e, r). A normalization constant of the light receiving part r with respect to the light emitter e is expressed as C(e, r). The normalization constant C(e, r) is determined by calibration. For example, at the time of measuring the pulse, the intensity of the reflected light received by the light receiving part r is corrected by the following Formula 1. M(e, r) is the normalized intensity of the reflected light. Each of the plurality of light receiving parts 120 is individually normalized for each light emitter 11.

$$M(e,r)=I(e,r)\times C(e,r) \quad (1)$$

Figure 7:
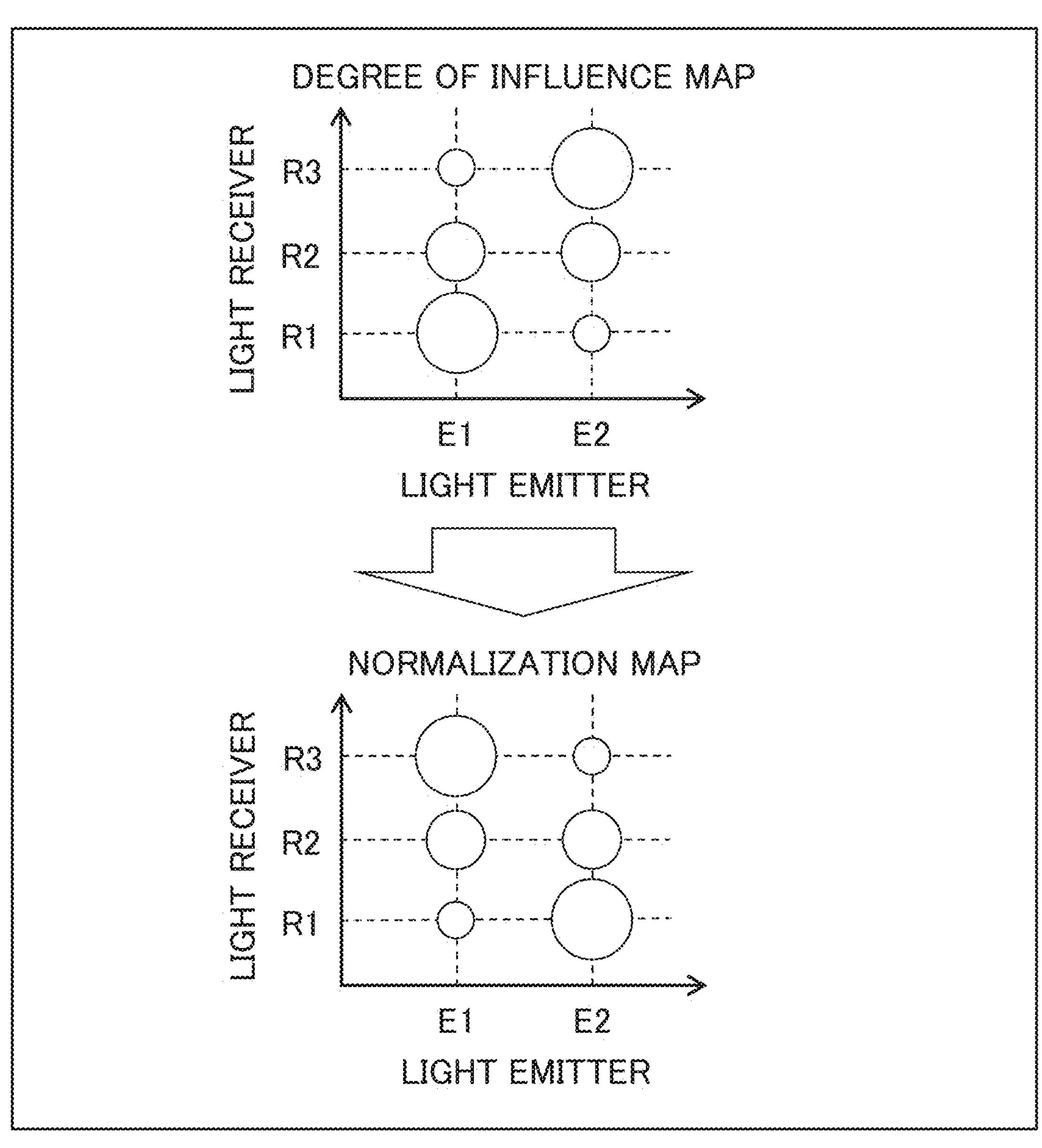
FIG. 7 is a conceptual diagram for describing an example of setting of a normalization constant by the pulse measurement device 15 according to the first example embodiment.

FIG. 7 is a conceptual diagram for describing the degree of influence of the light emitter 11 on the light receiving part 120 and normalization of the light receiving part 120 on the light emitter 11. The upper part of FIG. 7 (the upper side of the arrow) is a degree of influence map obtained by mapping the magnitude relationship regarding the degree of influence of each light emitter 11 on each light receiving part 120. The lower part of FIG. 7 (the lower side of the arrow) is a normalization map obtained by mapping the magnitude relationship regarding the normalization constant of each light receiving part 120 with respect to each light emitter 11. In the case of controlling the light intensity of the optical signal emitted from the light emitter 11, the normalization map of FIG. 7 can be regarded as a normalization map obtained by mapping the magnitude relationship regarding the normalization constant of each light receiving part 120 with respect to each light emitter 11. In the degree of influence map and the normalization constant map, the magnitude of each of the degree of influence and the normalization constant are expressed by the magnitude of the radius of the circle. In the degree of influence map and the normalization constant map, the larger the degree of influence or the normalization constant, the larger the radius of the circle, and the smaller the degree of influence or the normalization constant, the smaller the radius of the circle. The size of the circle indicating the magnitude relationship between the degree of influence and the normalization constant indicated in the degree of influence map and the normalization map conceptually indicates a relative magnitude relationship.

In FIG. 7, the degree of influence of the light emitter E1 on the light receiving part R1 is larger than that on the light receiving part R3. Therefore, in order to make the light intensity of the optical signal emitted from the light emitter E1 uniform between the light receiving part R1 and the light receiving part R3, it is only required to multiply a normalization constant of the light receiving part R3 larger than that of the light receiving part R1. In FIG. 7, the degree of influence of the light emitter E2 on the light receiving part R3 is larger than that on the light receiving part R1. Therefore, in order to make the light intensity of the optical signal emitted from the light emitter E2 uniform between the light receiving part R1 and the light receiving part R3, it is only required to multiply a normalization constant of the light receiving part R1 larger than that of the light receiving part R3. In FIG. 7, the degree of influence of the light emitter E1 on the light receiving part R2 is substantially the same as that of the light emitter E2 on the light receiving part R2. Therefore, the light intensity of the optical signal emitted from the light emitter E1 or the light emitter E2 may be obtained by multiplying a normalization constant (1) that is not changed in the light receiving part R2.

Figure 8:
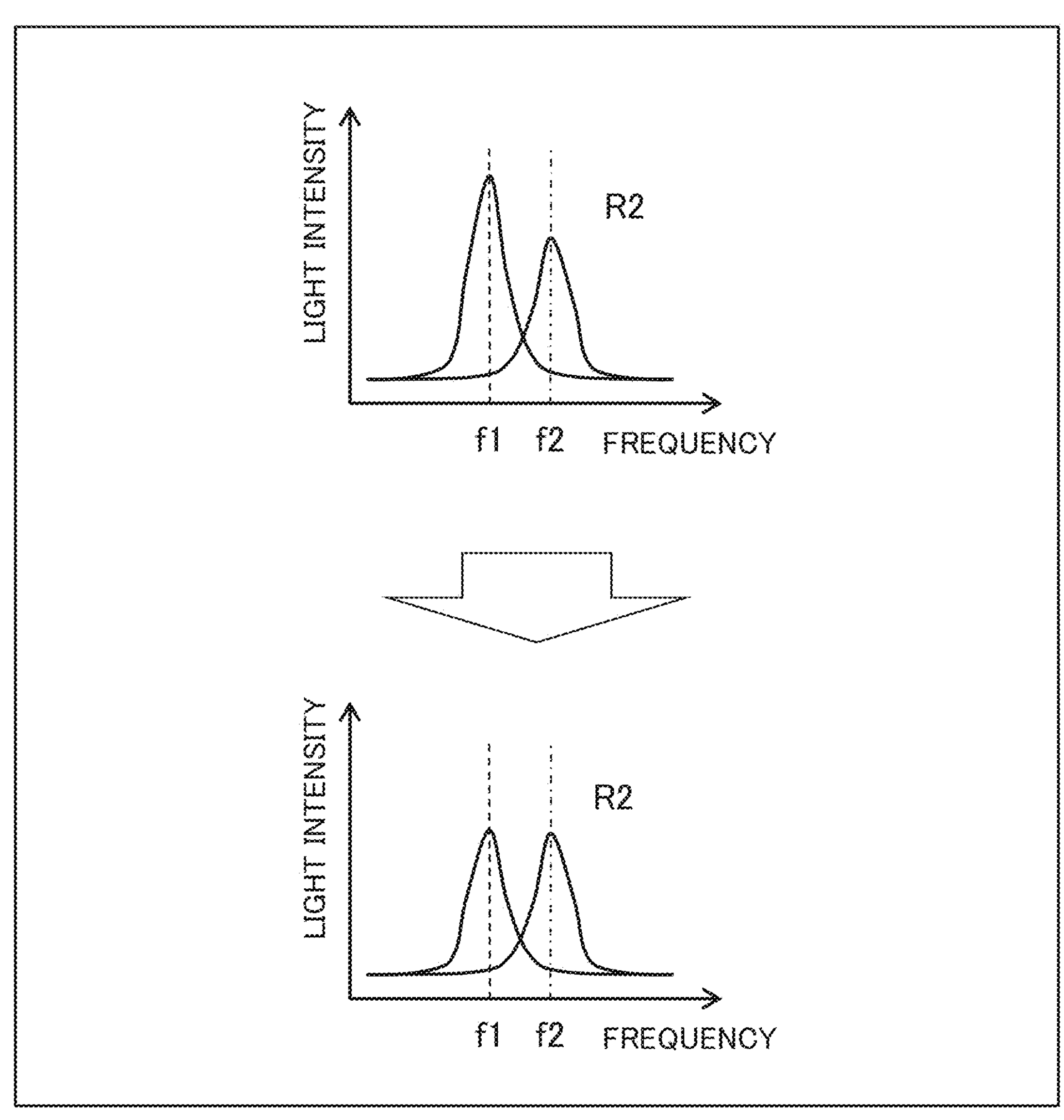
FIG. 8 is a conceptual diagram for describing an example of optimization of a reception signal by the pulse measurement device according to the first example embodiment.

FIG. 8 is a conceptual diagram for describing normalization of light intensity of reflected light in a case where optical signals emitted from a plurality of light emitters 11 are received by the same light receiving part 120 (light receiving part R2). The upper part of FIG. 8 (the upper side of the arrow) illustrates a waveform of the reflected light received by the light receiving part 120 (R2). The lower part of FIG. 8 (the lower side of the arrow) illustrates a waveform in which the reflected light received by the light receiving part 120 (R2) is normalized. In the example of FIG. 8, it is assumed that the light emitter E1 and the light emitter E2 emit optical signals having the same light intensity and different frequencies at the same timing. The light emitter E1 emits an optical signal having a frequency f1. The light emitter E2 emits an optical signal having a frequency f2. The light receiving part R2 receives reflected light of the optical signals emitted from the light emitter E1 and the light emitter E2 at the same timing. However, it is assumed that the difference in the light reception timing of the reflected light due to the difference between the distance between the light emitter E1 and the light receiving part R2 and the distance between the light emitter E2 and the light receiving part R2 is equal to or less than the detection limit.

As illustrated in FIG. 8, the reflected light of the optical signal emitted from the light emitter E1 and the reflected light of the optical signal emitted from the light emitter E2 are measured at different light intensity in the light receiving part R2 (upper part). In the present example embodiment, the light intensity of the reflected light is multiplied by a normalization constant that equalizes the degrees of influence of the plurality of light emitters 11 on each of the plurality of light receiving parts 120. As a result, the degree of influence of each of the plurality of light emitters 11 is uniform for each light receiving part 120, and the light intensity of the reflected light of the optical signals emitted from the light emitter E1 and the light emitter E2 is equal.

For example, in the example of FIG. 8, it is assumed that the degree of influence of the light emitter E1 is 2 with respect to the light receiving part R1, 1 with respect to the light receiving part R2, and 0.5 with respect to the light receiving part R3. In this case, the normalization constant is set for each of the plurality of light receiving parts 120 in such a way that the degree of influence of the light emitter E1 on the plurality of light receiving parts 120 is uniform. For example, in the example of FIG. 8, the normalization constant of the light emitter E1 is set to 0.5 with respect to the light receiving part R1, 1 with respect to the light receiving part R2, and 2 with respect to the light receiving part R3. When the normalization constant of each of the plurality of light emitters 11 set for each of the plurality of light receiving parts 120 is multiplied by the light intensity of the reflected light received by the plurality of light receiving parts 120, the influence of the plurality of light emitters 11 on each of the plurality of light receiving parts 120 can be made uniform. For example, the influence of each of the plurality of light emitters 11 on each of the plurality of light receiving parts 120 may be made uniform by adjusting the optical outputs of the plurality of light emitters 11 based on the normalization constant of each of the plurality of light emitters 11 set for each of the plurality of light receiving parts 120.

The control unit 13 individually controls each of the plurality of light emitters 11 and causes each of the plurality of light emitters 11 to emit an optical signal. For example, the control unit 13 collectively controls the plurality of light emitters 11 in such a way that optical signals having the same intensity are output from the plurality of light emitters 11. For example, the control unit 13 controls each of the plurality of light emitters 11 in such a way that an optical signal having individual intensity is output from each of the plurality of light emitters 11. For example, the control unit 13 may stop the operation of any one of the plurality of light emitters 11 depending on the situation. The control unit 13 controls the light emitter 11 under different conditions in the calibration period and the pulse measurement period.

In the calibration period, the control unit 13 controls the light emitter 11 in such a way that modulated light for calibration is emitted. The control unit 13 causes the plurality of light emitters 11 to emit modulated light of different frequencies. The modulated light emitted from the plurality of light emitters 11 is modulated at a specific frequency for each light emitter 11. Therefore, the light emitter 11 of the emission source of the modulated light related to the reflected light can be distinguished according to the frequency of the reflected light received by each of the plurality of light receiving parts 120.

The calibration is executed at a preset timing. For example, the calibration is executed at a timing when the pulse measurement device 10 is attached to the subject. For example, the calibration is executed when the pulse measurement device 10 is activated. For example, the calibration may be executed at a refresh timing set in advance. For example, the calibration may be set to be executed in response to a request of a user such as a subject. The timing of calibration can be set to any timing.

In the pulse measurement period, the control unit 13 controls the light emitter 11 in such a way that an optical signal for pulse measurement is emitted. The control unit 13 causes the plurality of light emitters 11 to emit optical signals having different frequencies. The optical signal emitted from each of the plurality of light emitters 11 is emitted at a specific frequency for each light emitter 11. Therefore, the light emitter 11 of the emission source of the optical signal related to the reflected light can be distinguished according to the frequency of the reflected light received by each of the plurality of light receiving parts 120.

The control unit 13 acquires a reception signal related to the reflected light received by each of the plurality of light receiving parts 120 from the plurality of light receiving parts 120. The reception signal has intensity related to the light intensity of the reflected light received by each of the plurality of light receiving parts 120. The control unit 13 processes the reception signal under different conditions in the calibration period and the pulse measurement period.

In the calibration period, the control unit 13 acquires the reception signal from the light receiving part 120 that has received the reflected light of the modulated light for calibration. The control unit 13 calculates the degree of influence of each of the plurality of light emitters 11 on each of the plurality of light receiving parts 120. The control unit 13 sets a normalization constant of each of the plurality of light emitters 11 related to each of the plurality of light receiving parts 120 based on the calculated degree of influence.

In the pulse measurement period, the control unit 13 acquires the reception signal from the light receiving part 120 that has received the reflected light of the optical signal for pulse measurement. The control unit 13 optimizes the intensity of the reception signal acquired from each of the plurality of light receiving parts 120. The control unit 13 optimizes the intensity of the reception signal by multiplying the intensity of the reception signal acquired from each of the plurality of light receiving parts 120 by a normalization constant set for each of the plurality of light receiving parts 120 for each of the plurality of light emitters 11.

The control unit 13 outputs a normalized signal (also referred to as a pulse signal). The control unit 13 may output the pulse signal via a wire such as a cable or may output the pulse signal via wireless communication. For example, the control unit 13 is configured to output a pulse signal via a wireless communication function (not illustrated) conforming to a standard such as Bluetooth (registered trademark) or WiFi (registered trademark). The communication function of the control unit 13 may conform to a standard other than Bluetooth (registered trademark) or WiFi (registered trademark). The output destination and application of the pulse signal are not particularly limited. For example, the control unit 13 transmits a pulse signal to a terminal device (not illustrated) connected to the pulse measurement device 10. For example, the control unit 13 transmits a pulse signal to a portable terminal (not illustrated) carried by the user who uses the pulse measurement device 10.

The substrate 14 is a bendable substrate. The substrate 14 has a bendable plate-like shape. For example, the substrate 14 has a structure in which a conductive layer such as a copper foil is formed on a face of a polyimide base layer, and the conductive layer is laminated with a covering layer of a plastic film. For example, the base layer and the covering layer of the substrate 14 may be mainly composed of a urethane nonwoven fabric, vinyl chloride, a stretchable cotton fabric, a sponge sheet, a urethane film, or an olefin film. The light emitter 11, the light receiving part 120, and the control unit 13 mounted on the substrate 14 may be configured to be deformed or may be configured not to be deformed according to the deformation of the substrate 14.

The plurality of light emitters 11 and the plurality of light receiving parts 120 are disposed on the measurement face of the substrate 14. An adhesive layer 17 is formed in a peripheral portion of the measurement face of the substrate 14. The portion where the adhesive layer 17 is formed may have a material or structure different from those of the other portions. For example, when the portion where the adhesive layer 17 is formed has a mesh-like structure, the portion of the adhesive layer 17 is less likely to be stuffy, and a decrease in adhesive force of the adhesive layer 17 due to sweat or the like can be suppressed. The control unit 13 is disposed on the second face facing the measurement face of the substrate 14. The control unit 13 may be disposed inside the substrate 14. For example, in order to improve the waterproof property, the control unit 13 may be disposed inside the substrate 14. For example, in order to improve the waterproof property, the control unit 13 may be covered with a waterproof film or the like. For example, when the pulse measurement device 10 is attached to the body of the subject, the substrate 14 is deformed according to the shape of the portion to be attached. The material, structure, and shape of the substrate 14 are not particularly limited.

The adhesive layer 17 is formed at a peripheral portion of the measurement face of the substrate 14. The adhesive layer 17 includes an adhesive for attaching the pulse measurement device 10 to the body of the subject. For example, the adhesive layer 17 includes an acrylic adhesive, a rubber adhesive, or a silicone adhesive. The adhesive layer 17 preferably has a light shielding property in such a way that light from the outside does not reach the light emitter 11 and the light receiving part 120. The material of the adhesive layer 17 is not particularly limited. For example, it is preferable to use a material that is less irritating to the skin for the adhesive layer 17. For example, the adhesive layer 17 may contain a substance that reduces discomfort to the skin. For example, the adhesive layer 17 may contain menthol or the like. For example, the adhesive layer 17 may contain a substance that suppresses a decrease in adhesive force due to absorption of moisture such as sweat. For example, the adhesive layer 17 may contain a polymer absorber or the like.

[Control Unit]

Next, a detailed configuration of the control unit 13 of the pulse measurement device 10 will be described. As illustrated in FIG. 1, the control unit 13 includes the light emission control unit 131, the signal acquisition unit 132, the normalization constant setting unit 133, the storage unit 134, the optimization unit 135, and the output unit 136.

The light emission control unit 131 controls the plurality of light emitters 11. The light emission control unit 131 individually controls each of the plurality of light emitters 11, and causes each of the plurality of light emitters 11 to emit an optical signal. For example, the light emission control unit 131 collectively controls the plurality of light emitters 11 in such a way that optical signals having the same intensity are output from the plurality of light emitters 11. For example, the light emission control unit 131 controls each of the plurality of light emitters 11 in such a way that an optical signal having an individual intensity is output from each of the plurality of light emitters 11. For example, the light emission control unit 131 may stop the operation of any one of the plurality of light emitters 11 depending on the situation.

The light emission control unit 131 controls the light emitter 11 under different conditions in the calibration period and the pulse measurement period. In the calibration period, the light emission control unit 131 controls the light emitter 11 in such a way that modulated light for calibration is emitted. In the calibration period, the light emission control unit 131 causes the plurality of light emitters 11 to emit modulated light having different frequencies. In the pulse measurement period, the light emission control unit 131 controls the light emitter 11 in such a way that an optical signal for pulse measurement is emitted. In the pulse measurement period, the light emission control unit 131 causes the plurality of light emitters 11 to emit optical signals having different frequencies. For example, in a case where each of the plurality of light emitters 11 is controlled based on the normalization constant, the light emission control unit 131 controls each light emitter 11 based on the normalization constant stored in the storage unit 134.

The signal acquisition unit 132 acquires a reception signal related to the reflected light received by each of the plurality of light receiving parts 120 from each of the plurality of light receiving parts 120. The reception signal reflects the light intensity of the reflected light received by each of the plurality of light receiving parts 120. The signal acquisition unit 132 processes reception signals under different conditions in the calibration period and the pulse measurement period. In the calibration period, the signal acquisition unit 132 acquires the reception signal from the light receiving part 120 that has received the reflected light of the modulated light for calibration. In the pulse measurement period, the signal acquisition unit 132 acquires the reception signal from the light receiving part 120 that has received the reflected light of the optical signal for pulse measurement.

In the calibration period, the normalization constant setting unit 133 acquires the reception signal based on the reflected light of the modulated light emitted from the plurality of light emitters 11 from each of the plurality of light receiving parts 120. The normalization constant setting unit 133 calculates the degree of influence of each of the plurality of light emitters 11 on each of the plurality of light receiving parts 120. The control unit 13 sets a normalization constant of each of the plurality of light emitters 11 related to each of the plurality of light receiving parts 120 based on the calculated degree of influence. The normalization constant setting unit 133 stores the set normalization constant in the storage unit 134. For example, the normalization constant setting unit 133 may store a normalization map in which the set normalization constant is mapped in the storage unit 134.

The storage unit 134 stores the normalization constant set by the normalization constant setting unit 133. For example, the storage unit 134 may store a normalization map in which the set normalization constant is mapped. The normalization constant stored in the storage unit 134 is referred to by the light emission control unit 131 and the optimization unit 135.

In the pulse measurement period, the optimization unit 135 acquires the reception signal based on the reflected light of the optical signals emitted from the plurality of light emitters 11 from each of the plurality of light receiving parts 120. The optimization unit 135 optimizes the intensity of the reception signal acquired from each of the plurality of light receiving parts 120. The optimization unit 135 optimizes the intensity of the reception signal by multiplying the intensity of the reception signal acquired from each of the plurality of light receiving parts 120 by a normalization constant set for each of the plurality of light receiving parts 120 for each of the plurality of light emitters 11. The signal normalized by the optimization unit 135 is a pulse signal.

The output unit 136 outputs a signal (also referred to as a pulse signal) normalized by the optimization unit 135. The output unit 136 may output the pulse signal via a wire such as a cable or may output the pulse signal via wireless communication. For example, the output unit 136 is configured to output a pulse signal via a wireless communication function (not illustrated) conforming to a standard such as Bluetooth (registered trademark) or WiFi (registered trademark). The communication function of the output unit 136 may conform to a standard other than Bluetooth (registered trademark) or WiFi (registered trademark). The output destination and application of the pulse signal are not particularly limited. For example, the output unit 136 outputs a pulse signal to a dedicated terminal device (not illustrated) having a screen. For example, the output unit 136 outputs a pulse signal to a portable terminal (not illustrated) such as a smartphone or a tablet carried by the user. For example, the output unit 136 outputs a pulse signal to an external system (not illustrated) constructed in a server or a cloud.

Figure 9:
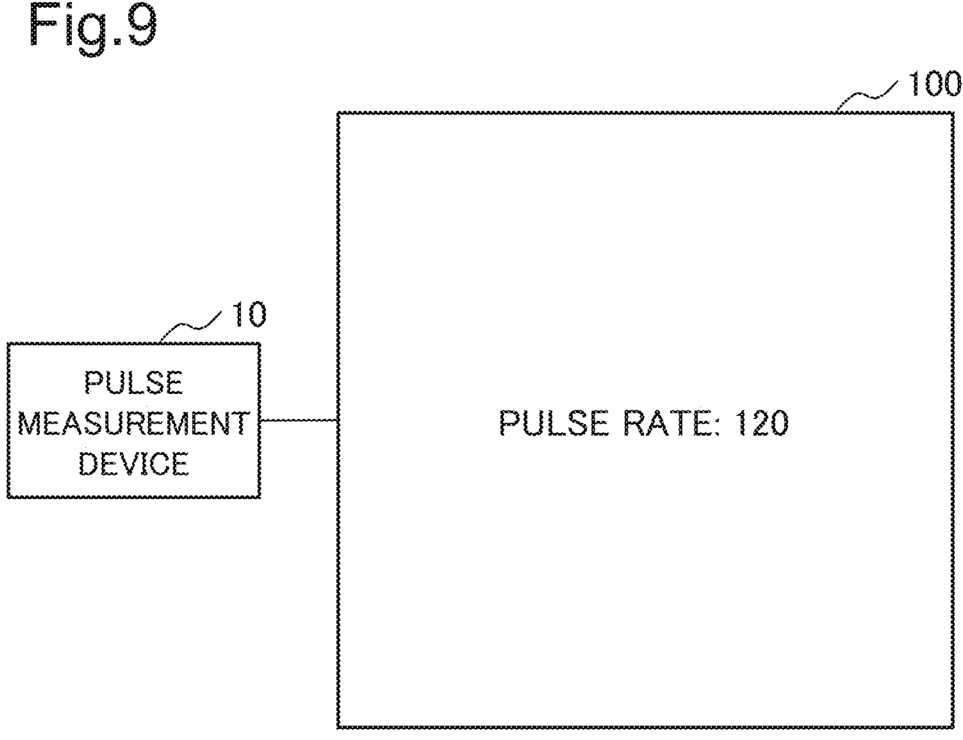
FIG. 9 is a conceptual diagram illustrating an example of displaying a pulse rate according to a pulse signal output from the pulse measurement device according to the first example embodiment.

FIG. 9 is an example in which the pulse rate measured according to the pulse signal output from the pulse measurement device 10 is displayed on the screen of a terminal device 100. The pulse rate corresponds to the number of pulsation (pulse) per unit time. The number of pulsations per minute is defined as a pulse rate. The user who has visually recognized the pulse rate displayed on the screen can confirm the pulse rate of the subject. For example, the physical condition or the like of the subject can be verified according to the pulse rate. The pulse is derived from the heartbeat of the heart. Therefore, the pulse rate corresponds to the heart rate. When the pulse rate of the subject can be measured/displayed in real time, the physical condition of the subject can be accurately monitored in real time. For example, the subjective exercise intensity of the subject can be quantified according to the values of the exercise heart rate and the resting heart rate. The quantified subjective exercise intensity or the fatigue level according to the subjective exercise intensity may be displayed on the screen of the terminal device 100.

Figure 10:
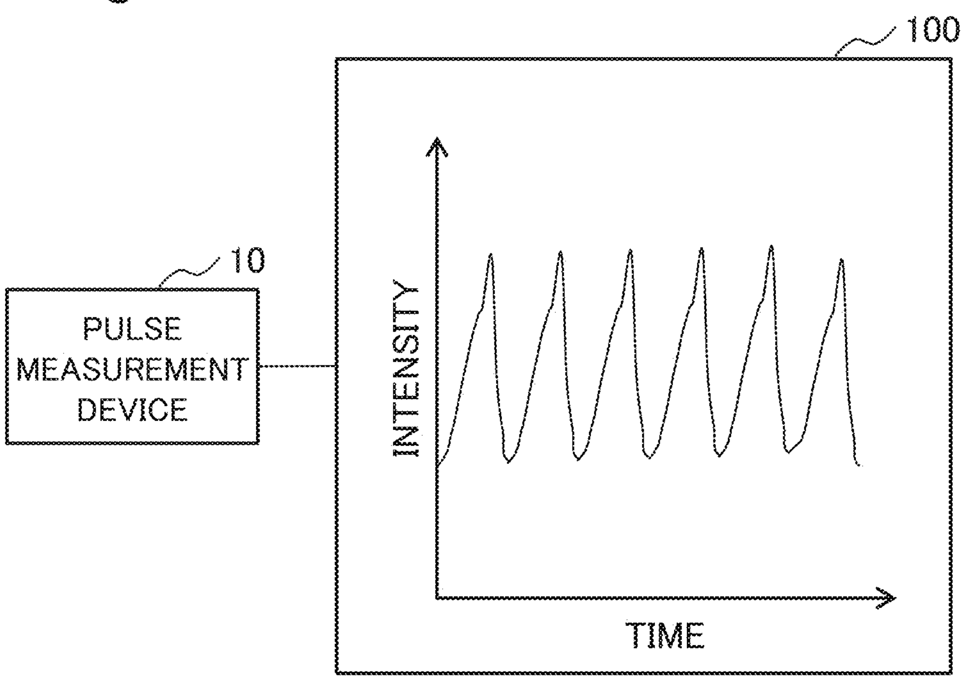
FIG. 10 is a conceptual diagram illustrating an example of displaying time-series data of a pulse signal output from the pulse measurement device according to the first example embodiment.

FIG. 10 illustrates an example in which the waveform of the time-series data of the signal output from the pulse measurement device 10 is displayed on the screen of the terminal device 100. The user who visually recognizes the waveform displayed on the screen can confirm the state of the pulse of the subject. For example, the state of the subject's body, health, mind, emotion, and the like can be verified based on the intensity, interval, and change over time of the pulse.

(Operation)

Next, an example of the operation of the pulse measurement device 10 according to the present example embodiment will be described with reference to the drawings. Hereinafter, an example of the operation of the pulse measurement device 10 will be described along a flowchart with the control unit 13 as an operation subject.

[Calibration 1]

Figure 11:
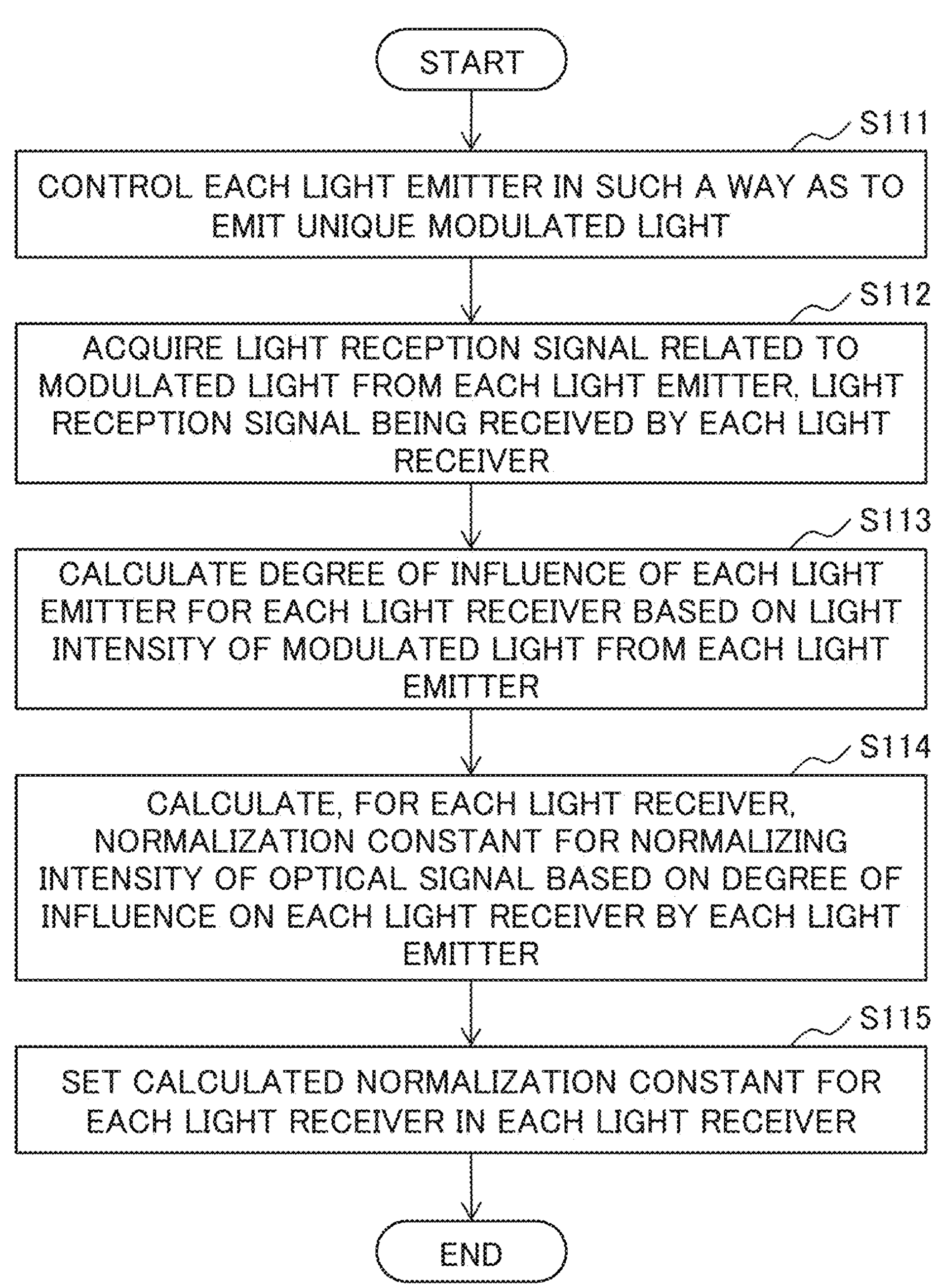
FIG. 11 is a flowchart for describing an example of calibration by the pulse measurement device according to the first example embodiment.

FIG. 11 is a flowchart for describing an example of the operation in the calibration period by the control unit 13 of the pulse measurement device 10. The flowchart of FIG. 11 is an example in which the plurality of light emitters 11 is operated simultaneously to perform calibration.

In FIG. 11, first, the control unit 13 controls each of the plurality of light emitters 11 in such a way as to emit unique modulated light (step S111). In a case where calibration is performed by operating the plurality of light emitters 11 at the same time, the control unit 13 causes the plurality of respective light emitters 11 to emit unique modulated light having different frequencies.

The control unit 13 acquires a reception signal related to the modulated light from each of the plurality of light emitters 11, the reception signal being received by each of the plurality of light receiving parts 120 (step S112).

The control unit 13 calculates the degree of influence of the plurality of light emitters 11 on each light receiving part 120 based on the light intensity of the modulated light from the plurality of light emitters 11 (step S113). The light intensity of the modulated light is reflected on the intensity of the reception signal related to the modulated light received by the light receiving part 120.

The control unit 13 calculates a normalization constant for normalizing the light intensity of the optical signal for each light receiving part 120 based on the degree of influence of each of the plurality of light emitters 11 on the plurality of light receiving parts 120 (step S114).

The control unit 13 sets the calculated normalization constant for each light receiving part 120 in each of the plurality of light receiving parts 120 (step S115). In the case of adjusting the optical output of the light emitter 11, the control unit 13 sets the calculated normalization constant for each light receiving part 120 in each of the plurality of light emitters 11.

[Calibration 2]

Figure 12:
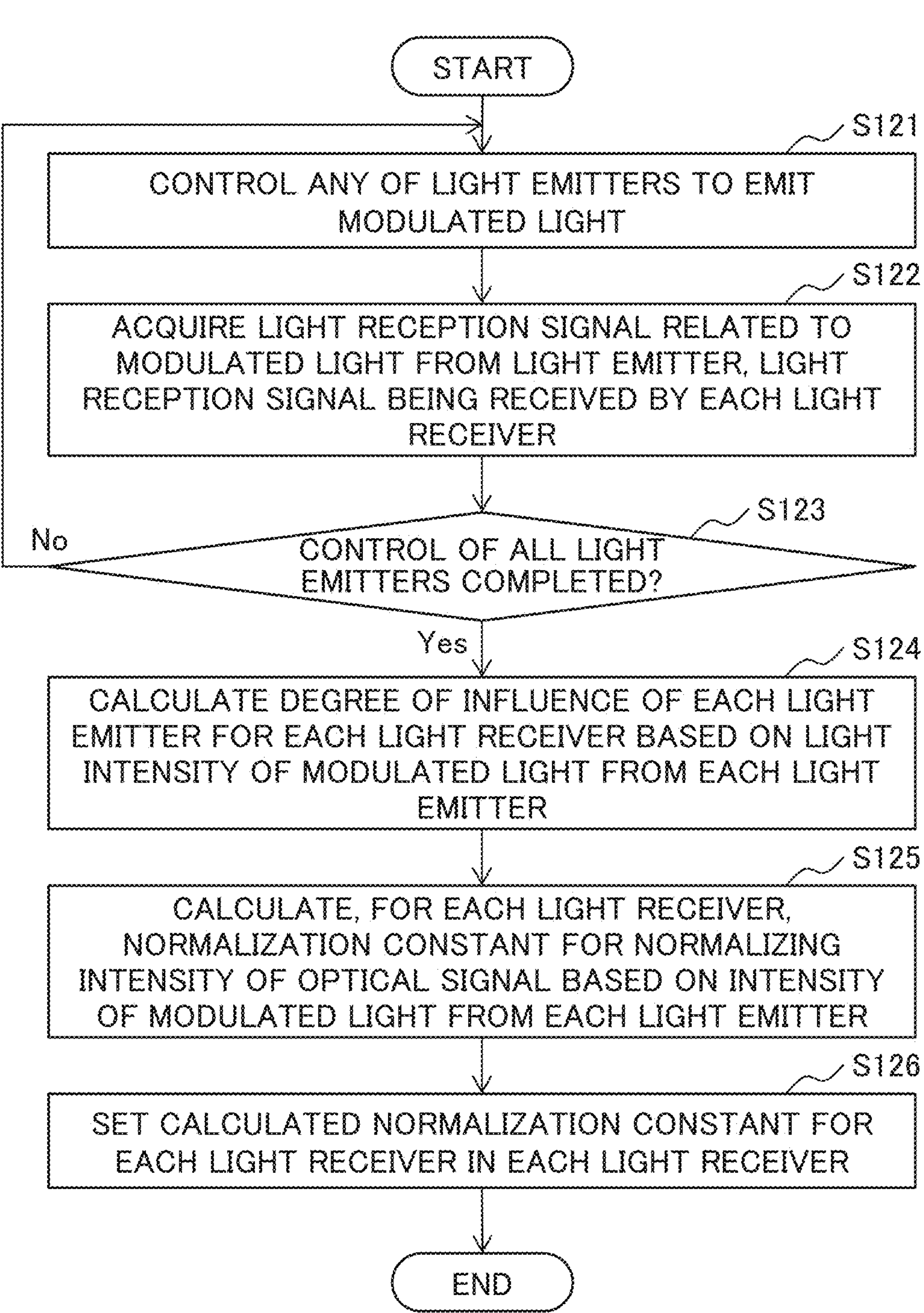
FIG. 12 is a flowchart for describing another example of calibration by the pulse measurement device according to the first example embodiment.

FIG. 12 is a flowchart for describing another example of the operation in the calibration period by the control unit 13 of the pulse measurement device 10. The flowchart of FIG. 12 is an example in which the plurality of light emitters 11 is operated one by one to perform calibration.

In FIG. 12, first, control unit 13 controls one of the plurality of light emitters 11 to emit modulated light (step S121). When calibration is performed by operating the plurality of light emitters 11 one by one, the frequencies of the modulated light emitted from the plurality of light emitters 11 may be the same.

The control unit 13 acquires a reception signal related to the modulated light from the operating light emitter 11, the reception signal being received by each of the plurality of light receiving parts 120 (step S122).

When the control of all the plurality of light emitters 11 is completed (Yes in step S123), the control unit 13 calculates the degree of influence of the plurality of light emitters 11 on each light receiving part 120 based on the light intensity of the modulated light from the plurality of light emitters 11. The light intensity of the modulated light is reflected on the intensity of the reception signal related to the modulated light received by the light receiving part 120. When the control of all the plurality of light emitters 11 is not completed (No in step S123), the process returns to step S121.

The control unit 13 calculates a normalization constant for normalizing the light intensity of the optical signal for each light receiving part 120 based on the degree of influence of each of the plurality of light emitters 11 on the plurality of light receiving parts 120 (step S125).

The control unit 13 sets the calculated normalization constant for each light receiving part 120 in each of the plurality of light receiving parts 120 (step S126). In the case of adjusting the optical output of the light emitter 11, the control unit 13 sets the calculated normalization constant for each light receiving part 120 in each of the plurality of light emitters 11.

[Pulse Measurement]

Figure 13:
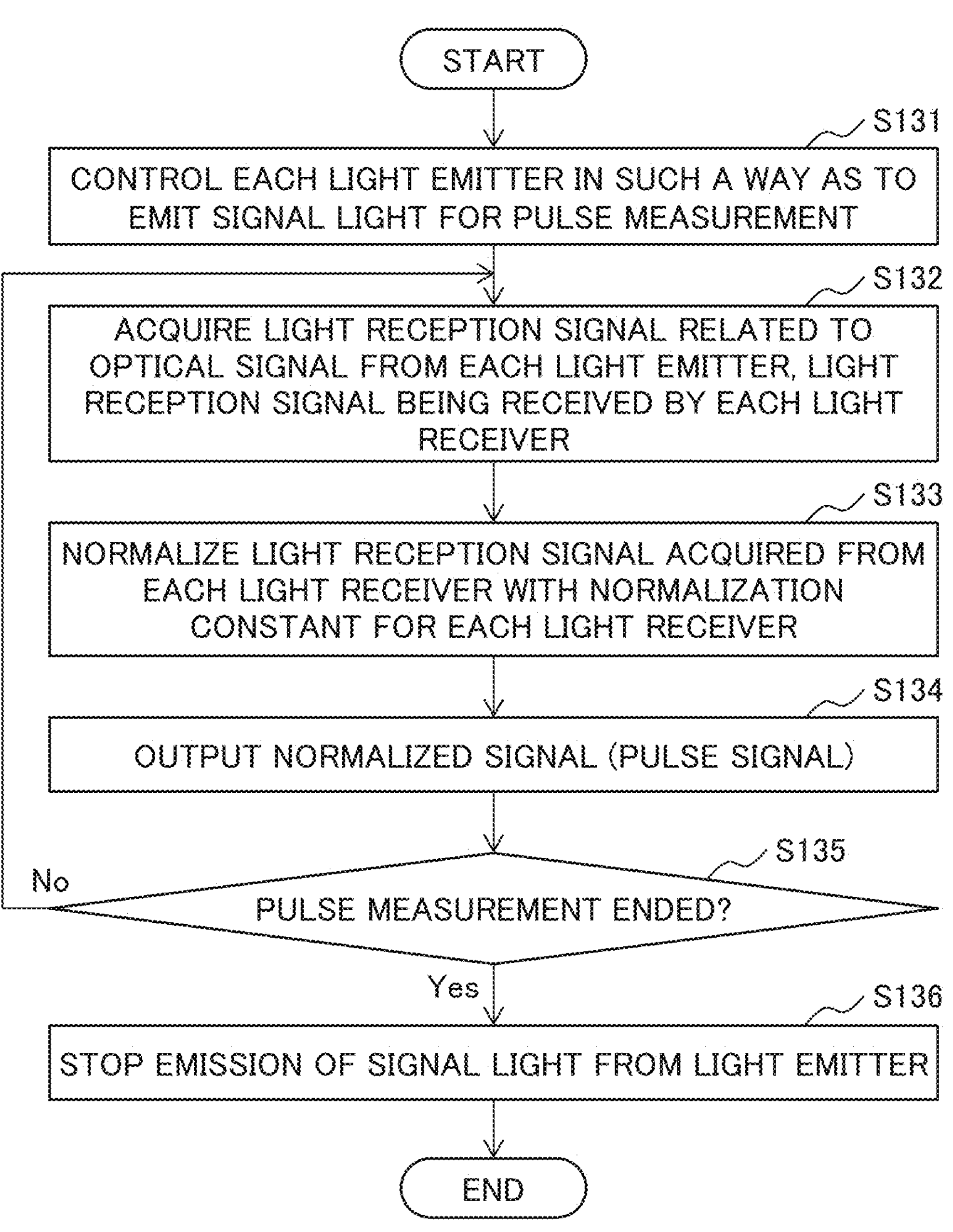
FIG. 13 is a flowchart for describing an example of pulse measurement by the pulse measurement device according to the first example embodiment.

FIG. 13 is a flowchart for describing an example of the operation in the pulse measurement period by the control unit 13 of the pulse measurement device 10. The flowchart of FIG. 13 relates to a pulse measurement period in a stage where calibration related to the plurality of light receiving parts 120 is completed.

In FIG. 13, first, the control unit 13 controls each of the plurality of light emitters 11 in such a way as to emit an optical signal for pulse measurement (step S131). In the case of adjusting the optical output of the light emitter 11, the control unit 13 adjusts the optical output of each of the plurality of light emitters 11 according to the normalization constant of each light receiving part 120.

Next, the control unit 13 acquires a reception signal related to the reflected light of the optical signal from each of the plurality of light emitters 11, the reception signal being received by each of the plurality of light receiving parts 120 (step S132).

Next, the control unit 13 optimizes the reception signal acquired from each of the plurality of light receiving parts 120 with a normalization constant for each light receiving part 120 (step S133).

Next, the control unit 13 outputs a normalized signal (pulse signal) (step S134). For example, the control unit 13 outputs a pulse signal to a terminal device, a portable terminal, an external system, a display device, or the like (not illustrated).

When ending the pulse measurement (Yes in step S135), the control unit 13 stops the emission of the optical signals from the plurality of light emitters 11 (step S136). When the pulse measurement is continued (No in step S135), the process returns to step S132. For example, the end/continuation of the pulse measurement is determined according to a preset schedule. For example, the end/continuation of the pulse measurement may be set at an any timing according to the input operation of the user.

[Related Art]

Figure 14:
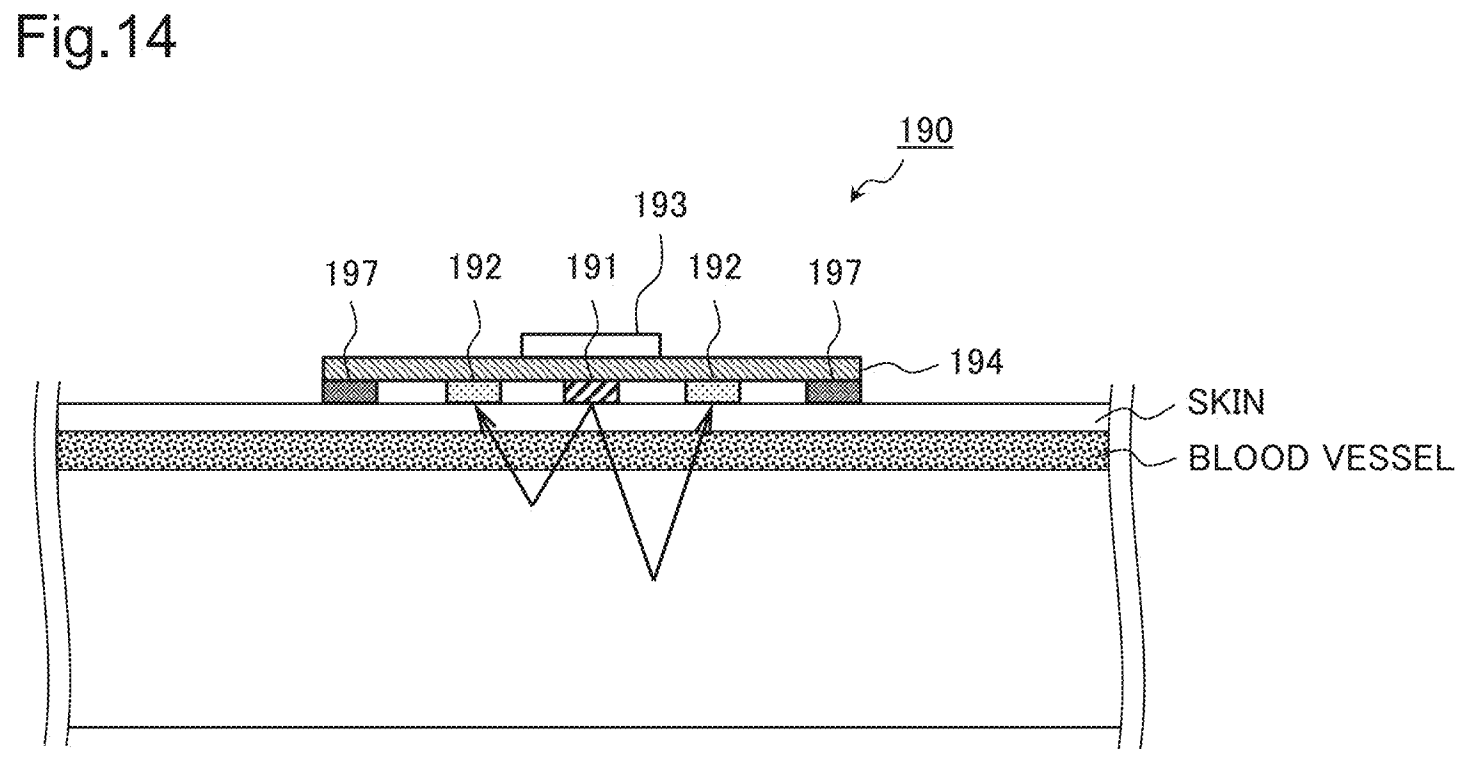

A pulse measurement device according to a related art will be described with reference to the drawings. The related art is a comparative example of the first example embodiment. FIG. 14 is a conceptual diagram illustrating an example of a configuration of a pulse measurement device 190 according to the related art. FIG. 14 is a cross-sectional view of the pulse measurement device 190. The pulse measurement device 190 includes a light emitter 191, a control unit 193, a plurality of light receivers 192, a substrate 194, and an adhesive layer 197. The arrangement and functions of the light emitter 191, the control unit 193, the plurality of light receivers 192, the substrate 194, and the adhesive layer 197 are similar to those in the first example embodiment. FIG. 14 illustrates a state in which the optical signal emitted from the light emitter 191 is reflected/scattered under the skin (in the body) of the subject.

Figure 15:
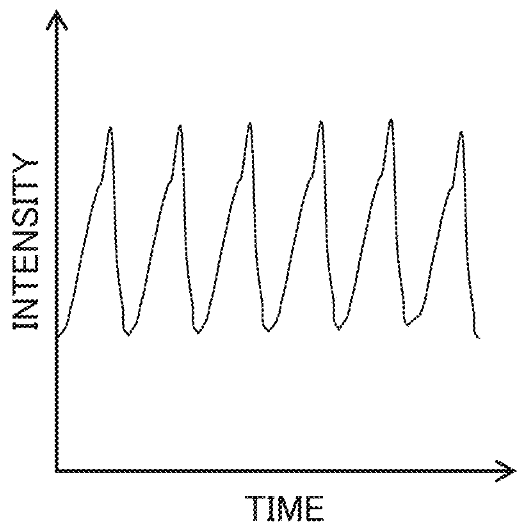
FIG. 15 is a conceptual diagram illustrating an example of a signal measured by a pulse measurement device according to the related art.
Figure 16:
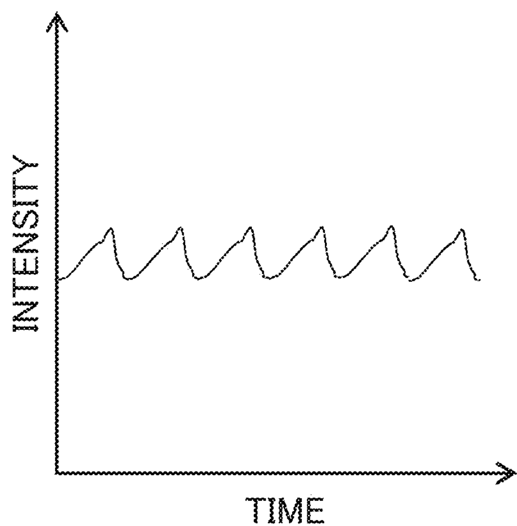
FIG. 16 is a conceptual diagram illustrating another example of a signal measured by the pulse measurement device according to the related art.

Each of FIGS. 15 to 16 is an example of a waveform of a pulse signal related to reflected light of the optical signal emitted from the light emitter 191, the pulse signal being received by each of the plurality of light receivers 192. FIG. 15 is an example in which the optical path of the optical signal is short and attenuation of the optical signal is small, compared with that in FIG. 16. FIG. 16 is an example in which the optical path of the optical signal is long and attenuation of the optical signal is large, compared with that in FIG. 15. The reflected light of the optical signal emitted from the light emitter 191 is received with different light intensity in each of the plurality of light receivers 192. In the related art, the light intensity of the reflected light received by each of the plurality of light receivers 192 is not normalized. The influence on the AC component of the pulse differs for each light receiving part 120 according to the position of the capillary vessel or the blood vessel under the skin to which the pulse measurement device 190 is attached. Therefore, in the technique of the related art, a different pulse signal is obtained for each light receiver 192 according to the environment under the skin.

Figure 17:
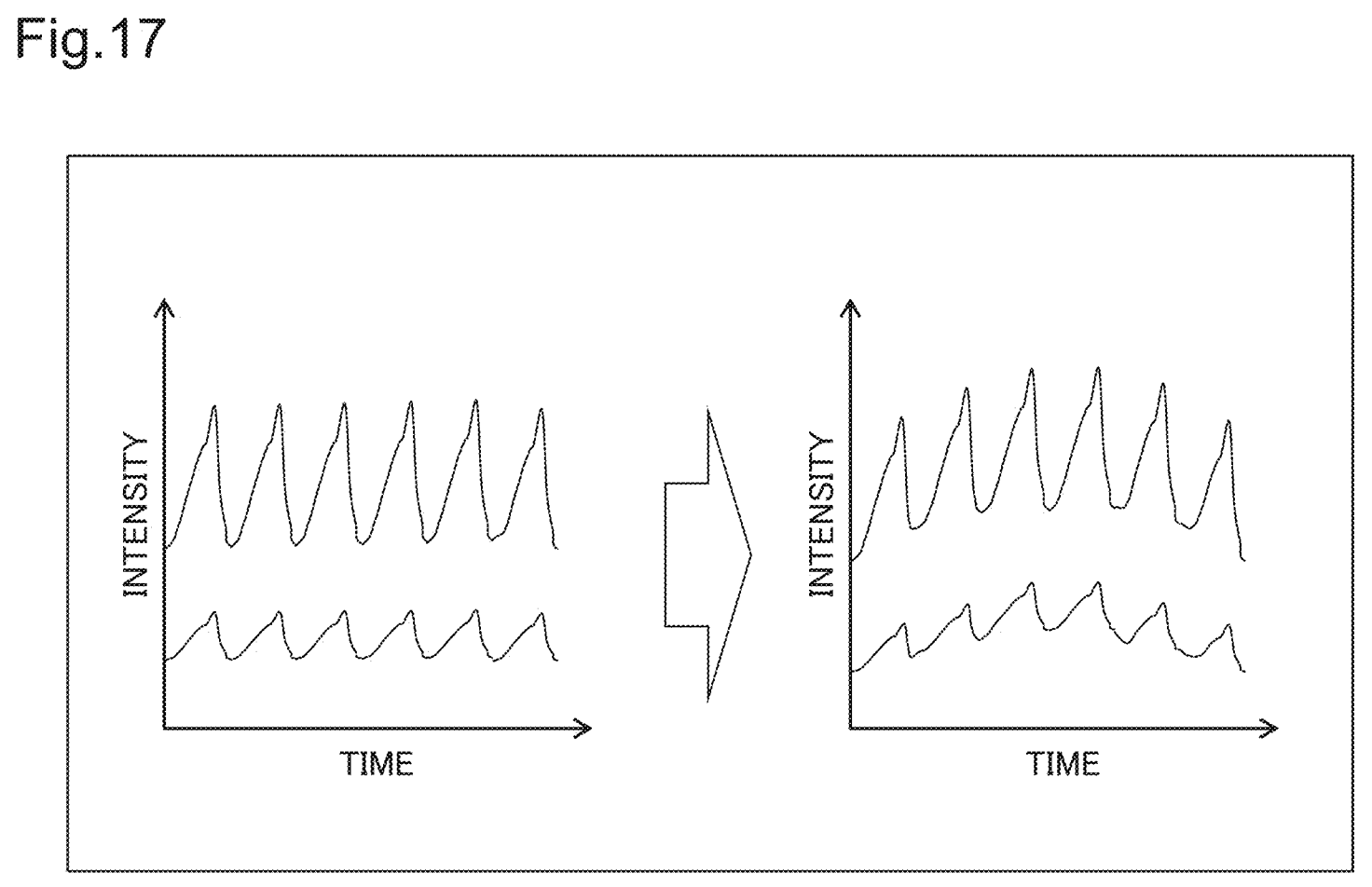

FIG. 17 is a conceptual diagram illustrating an example of distortion generated in the waveform of the pulse signal according to the body motion of the subject. The variation due to the body motion appears as a variation of the DC component of the reflected light received by each of the plurality of light receivers 192. In other words, the variation due to the body motion is a variation factor of the baseline of the pulse. In the related art method, the baseline of the pulse fluctuates according to the body motion of the subject.

In the related art method, the pulse signal obtained for each light receiver 192 varies depending on the environment under the skin, and the influence of the body motion of the subject, the difference in optical path of the optical signal from the light emitter 191 to the light receiver 192, and the like. The pulse signal of each light receiver 192 can be corrected by software. However, in a case where the light emitter 191 is single, it is difficult to accurately correct the AC component and the DC component included in the pulse signal by correction using software.

On the other hand, in the method of the first example embodiment, the normalization constant for each of the plurality of light emitters 11 is set for each of the light receiving parts 120 based on the degree of influence of each of the plurality of light emitters 11 on each of the plurality of light receiving parts 120. Therefore, according to the method of the first example embodiment, since the light intensity of the reflected light of the optical signals received by the plurality of light receiving parts 120 is made uniform for each of the plurality of light emitters 11, the AC component and the DC component included in the pulse signal can be accurately corrected.

As described above, the pulse measurement device includes the plurality of light emitters, the light receiver, and the control unit. The plurality of light emitters is disposed on a measurement face of a substrate attached to the skin of the subject to be subjected to pulse measurement. The plurality of light emitters emits light toward the skin of the subject. The light receiver is disposed on the measurement face of the substrate. The light receiver includes a plurality of light receiving parts that receives reflected light of light emitted from the plurality of light emitters. The control unit causes the plurality of light emitters to emit light. The control unit receives a reception signal related to reflected light of light received by the light receiver from the light receiver. The control unit optimizes the intensity of the reception signal using the normalization constant set for each of the plurality of light emitters. The control unit outputs the reception signal whose intensity is optimized using the normalization constant as a pulse signal.

The pulse measurement device of the present example embodiment normalizes the intensity of the reception signal related to the reflected light reflected/scattered inside the human body of the light emitted from the plurality of light emitters toward the human body for each light emitter. According to the present example embodiment, the pulse of the subject can be accurately measured by uniformly normalizing the intensity of the reception signal according to the reflected light of the light emitted from the plurality of light emitters.

In an aspect of the present example embodiment, the control unit optimizes the optical output of each of the plurality of light emitters according to the normalization constant set for each of the plurality of light emitters. According to the present aspect, by optimizing the optical output of each of the plurality of light emitters, the intensity of the reception signal according to the reflected light of the light emitted from the plurality of light emitters can be optimized for each light receiving part, so that the pulse of the subject can be accurately measured.

In an aspect of the present example embodiment, the control unit causes each of the plurality of light emitters to emit modulated light modulated at a specific frequency in the calibration period. The control unit calculates the degree of influence of each of the plurality of light emitters on each of the plurality of light receiving parts according to the received light intensity of the reflected light of the modulated light for each light emitters in each of the plurality of light receiving parts included in the light receiver. The control unit sets, in each of the plurality of light receiving parts, the normalization constant by which the intensity of the reception signal according to the reflected light of the modulated light emitted from each of the plurality of light emitters is uniform according to the degree of influence calculated for each light emitter for each of the plurality of light receiving parts. According to the present aspect, the normalization constant for each of the plurality of light emitters can be set for each light receiving part.

In an aspect of the present example embodiment, the control unit causes each of the plurality of light emitters to emit an optical signal in the pulse measurement period. The control unit optimizes the intensity of the reception signal by multiplying the reception signal related to the reflected light of the optical signal for each of the plurality of light emitters, the optical signal being acquired from each of the plurality of light receiving parts, by the normalization constant for each of the plurality of light emitters set for each of the plurality of light receiving parts. According to the present aspect, the pulse of the subject can be accurately measured by setting the normalization constant for each of the plurality of light emitters for each light receiving part.

Second Example Embodiment

Next, a pulse measurement device according to a second example embodiment will be described with reference to the drawings. The pulse measurement device of the present example embodiment includes a light receiving element array in which a plurality of light receiving elements is arrayed instead of the plurality of light receivers. The light receiving element array is one form of a light receiver.

(Configuration)

FIG. 18 is a block diagram illustrating an example of a configuration of a pulse measurement device 20 according to the present example embodiment. The pulse measurement device 20 includes a plurality of light emitters 21-1 to m, a light receiving element array 22, and a control unit 23 (m is a natural number equal to or more than 2). A plurality of light receiving parts is disposed on the light receiving face of the light receiving element array 22. The control unit 23 includes a light emission control unit 231, a signal acquisition unit 232, a normalization constant setting unit 233, a storage unit 234, an optimization unit 235, and an output unit 236. Hereinafter, in a case where a matter common to the plurality of light emitters 21-1 to m is described, they may be referred to as a light emitter 21.

Figure 19:
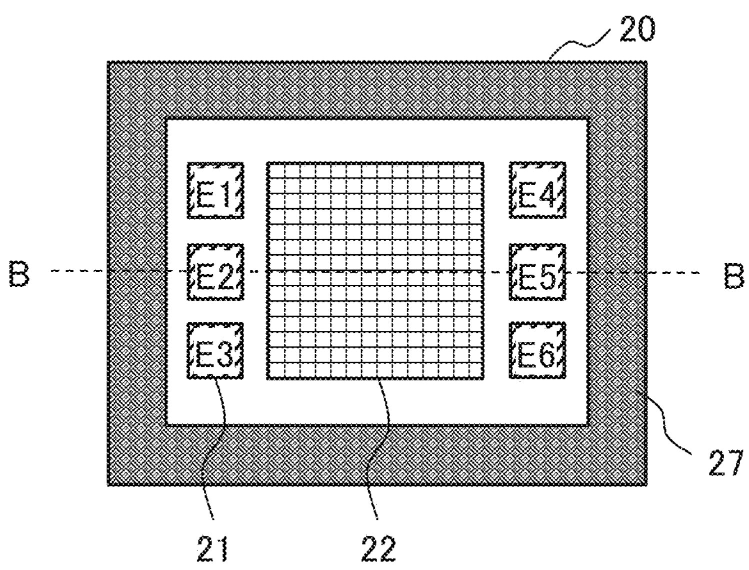
FIG. 19 is a conceptual diagram of the pulse measurement device according to the second example embodiment viewed from a measurement face side.
Figure 20:
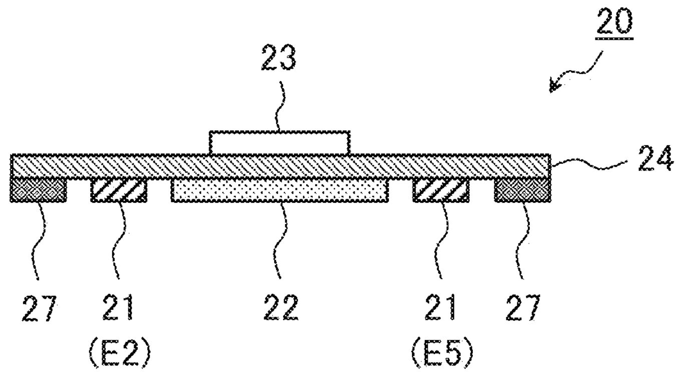
FIG. 20 is a cross-sectional view for describing a configuration of a pulse measurement device according to the second example embodiment.

FIG. 19 is a conceptual diagram of a measurement face of the pulse measurement device 20. FIG. 20 is a cross-sectional view of the pulse measurement device 20 taken along line B-B in FIG. 19. Hereinafter, an example in which the pulse measurement device 20 includes six light emitters 21 will be described. FIGS. 19 and 20 illustrate an example in which six light emitters 21 and one light receiving element array 22 are disposed on the same face (also referred to as a measurement face) of a substrate 24. An adhesive layer 27 for attaching the pulse measurement device 20 to the skin of the subject is installed in a peripheral portion in the measurement face of the substrate 24. The pulse measurement device 20 is attached to the skin of the subject in such a way that light from the outside does not enter the measurement face side of the substrate 24 in a state of being attached to the skin.

The light emitter 21 has a configuration similar to that of the light emitter 11 of the first example embodiment. The plurality of light emitters 21 is disposed in such a way that their emission faces face the same direction. The emission faces of the plurality of light emitters 21 and the light receiving face of the light receiving element array 22 are disposed in the same direction. The emission face of the light emitter 21 is directed to the skin of the subject in a state where the pulse measurement device 20 is attached to the skin of the subject.

The light receiving element array 22 has a light receiving face that receives reflected light of the optical signal emitted from the light emitter 21. The reflected light is a light component that is reflected/scattered under the skin (inside the body) of the subject and reaches the light receiving face of the light receiving element array 22 in the optical signal emitted from the light emitter 21. On the light receiving face of the light receiving element array 22, a plurality of light receiving parts is disposed in a two-dimensional array. For example, about 10,000 light receiving parts are disposed in a two-dimensional array on the light receiving face of the light receiving element array 22. The light intensity of the reflected light received by each of the plurality of light receiving parts disposed in a two-dimensional array is measured in association with the positions (addresses) of the light receiving parts.

For example, the light receiving element array 22 can be achieved by a sheet type image sensor disclosed in NPL 1 (NPL 1: T. Yokota, et al., "A conformable imager for biometric authentication and vital sign measurement", Nature Electronics, volume 3, p.p. 113-121 (2020)). The sheet type image sensor of NPL 1 has a configuration in which an organic photodiode, a thin-film transistor, a complementary metal-oxide semiconductor (CMOS), and a light detector are combined. In the present example embodiment, the light emitter 21 and the light receiving element array 22 are configured separately, but the light emitter 21 and the light receiving element array 22 may be integrated as in the sheet-type image sensor of NPL 1.

The reflected light of the optical signal emitted from each of the plurality of light emitters 21 is received by each of the plurality of light receiving parts disposed on the light receiving face of the light receiving element array 22 via different paths. The light intensity of the optical signal emitted from each of the plurality of light emitters 21 changes according to light absorption characteristics and scattering characteristics by body constituent tissues such as skin, blood vessels, muscles, fat, and bone. Therefore, the light intensity of the reflected light received by the light receiving element array 22 varies according to the length of the path, the environment under the skin, and the body motion of the subject. In the present example embodiment, an optical signal is emitted from the light emitter 21 from above the skin of the subject toward the body, and the pulse of the subject is measured according to reflected light of the optical signal. In the present example embodiment, a variation in the blood volume in the body due to pulsation is measured as a change in absorbance (also referred to as a light intensity change).

Figure 21:
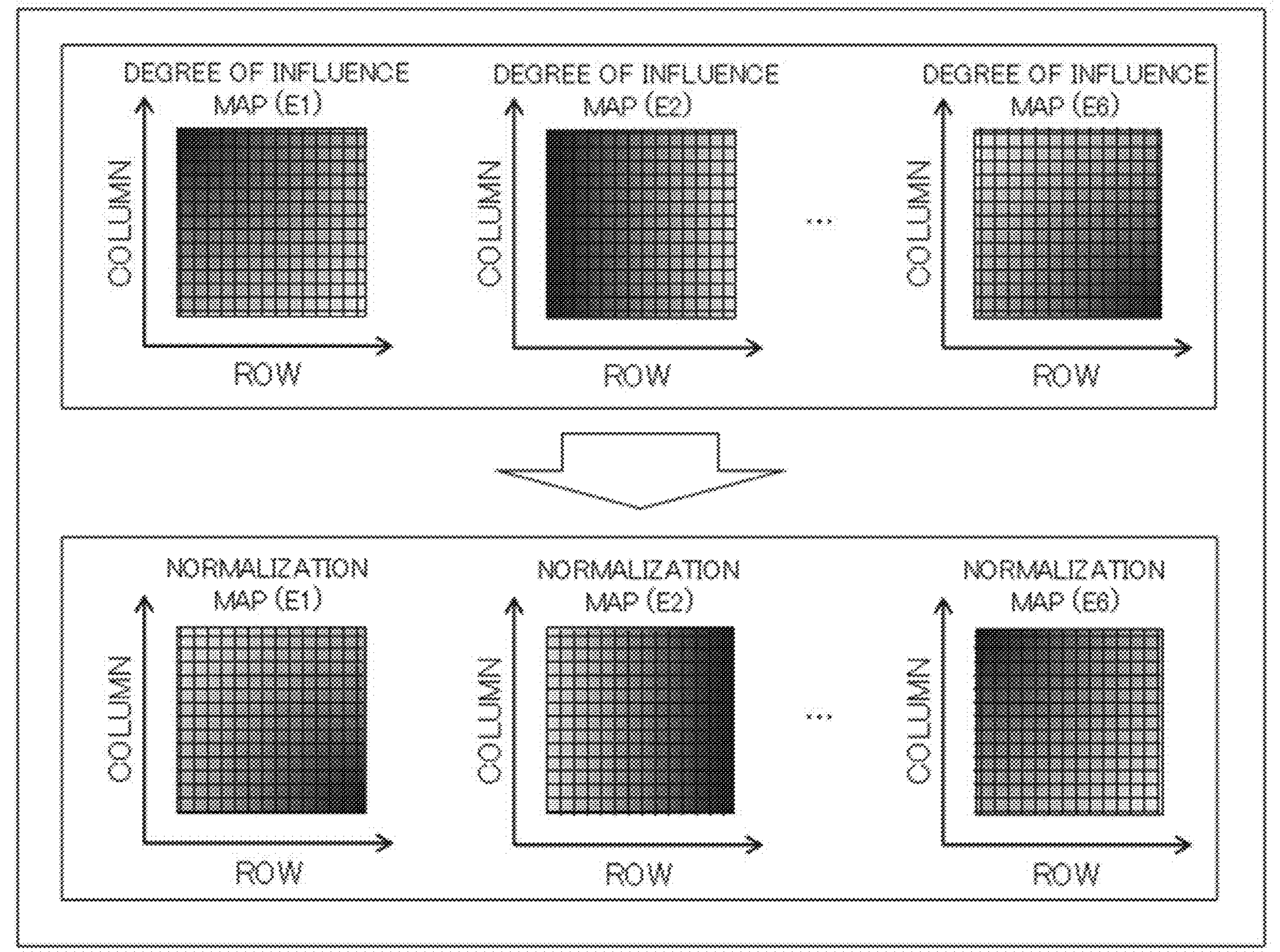
FIG. 21 is a conceptual diagram for describing an example of setting of a normalization constant by the pulse measurement device according to the second example embodiment.

FIG. 21 is a conceptual diagram for describing the degree of influence of each of the plurality of light emitters 21 on the plurality of light receiving parts disposed on the light receiving face of the light receiving element array 22 and the normalization of the light receiving part with respect to the light emitter 21. FIG. 21 illustrates an example of six light emitters 21-1 to 6 related to the configuration of FIG. 19. In FIG. 21, each of the plurality of light emitters 21-1 to 6 is denoted as a light emitter E1, a light emitter E2, . . . , and a light emitter E6. In FIG. 21, examples of the light emitter E3, the light emitter E4, and the light emitter E5 are omitted.

The upper part of FIG. 21 (the upper side of the arrow) is a degree of influence map obtained by mapping the magnitude relationship regarding the degree of influence of each light emitter 21 on the plurality of light receiving parts disposed on the light receiving face of the light receiving element array 22. The lower part of FIG. 21 (the lower side of the arrow) is a normalization map obtained by mapping the magnitude relationship regarding the normalization constant of the plurality of light receiving parts disposed on the light receiving face of the light receiving element array 22 with respect to each light emitter 21. In the case of controlling the light intensity of the optical signal emitted from the light emitter 21, the normalization map of FIG. 21 can be regarded as a normalization map obtained by mapping a magnitude relationship regarding a normalization constant for each light emitter 21 with respect to a plurality of light receiving parts disposed on the light receiving face of the light receiving element array 22. In the degree of influence map and the normalization map, the magnitudes of the degree of influence and the normalization constant are expressed by shading. In the degree of influence map and the normalization map, expression is made in such a way that the larger the degree of influence or the normalization constant, the thicker the degree of influence or the normalization constant, and the smaller the degree of influence or the normalization constant, the thinner the degree of influence or the normalization constant. Shading indicating a magnitude relationship of the degree of influence and the normalization constant indicated in the degree of influence map and the normalization map, respectively, conceptually indicates a relative magnitude relationship. In FIG. 21, the magnitudes of the degree of influence and the normalization constant are expressed by gradation of shading. In practice, since the degree of influence and the normalization constant are set for each of the plurality of light receiving parts disposed on the light receiving face, the degree of influence map and the normalization map are mosaic-like maps.

In FIG. 21, the degree of influence of the light emitter E1 is large at the upper left of the light receiving face, and gradually decreases from the upper left to the lower right of the light receiving face. Therefore, in order to make the light intensity of the optical signal emitted from the light emitter E1 uniform within the surface of the light receiving face of the light receiving element array 22, it is only required to multiply a normalization constant for the light receiving part at the lower right position of the light receiving face that is larger than that for the light receiving part at the upper left position of the light receiving face. Regarding the light emitter E1, the normalization constant gradually increases from the upper left position to the lower right position of the light receiving face. The degree of influence of the light emitter E2 is large on the left side of the light receiving face, and gradually decreases from the left side to the right side of the light receiving face. Therefore, in order to make the light intensity of the optical signal emitted from the light emitter E2 uniform within the surface of the light receiving face of the light receiving element array 22, it is only required to multiply a normalization constant for the light receiving part at the position on the right side of the light receiving face that is larger than that for the light receiving part at the position on the left side of the light receiving face. Regarding the light emitter E2, the normalization constant gradually increases from the position on the left side to the position on the right side of the light receiving face. Furthermore, the degree of influence of the light emitter E6 increases at the lower right of the light receiving face, and gradually decreases from the lower right to the upper left of the light receiving face. Therefore, in order to make the light intensity of the optical signal emitted from the light emitter E6 uniform in the surface of the light receiving face of the light receiving element array 22, it is only required to multiply a normalization constant for the light receiving part at the upper left position of the light receiving face that is larger than that for the light receiving part at the lower right position of the light receiving face. Regarding the light emitter E6, the normalization constant gradually increases from the lower right position to the upper left position of the light receiving face. As in the light emitter E1 and the like, the normalization constant is set for the other light emitters 21 (E3, E4, E5).

The control unit 23 has a configuration similar to that of the control unit 13 of the first example embodiment. The control unit 23 controls the plurality of light emitters 21. The control unit 23 individually controls each of the plurality of light emitters 21 and causes each of the plurality of light emitters 21 to emit an optical signal. For example, the control unit 23 collectively controls the plurality of light emitters 21 in such a way that optical signals having the same intensity are output from the plurality of light emitters 21. For example, the control unit 23 controls each of the plurality of light emitters 21 in such a way that an optical signal having an individual intensity is output from each of the plurality of light emitters 21. For example, the control unit 23 may stop the operation of any one of the plurality of light emitters 21 depending on the situation. The control unit 23 controls the light emitter 21 under different conditions in the calibration period and the pulse measurement period. The control of the light emitter 21 in the calibration period and the pulse measurement period is similar to that in the first example embodiment.

The control unit 23 acquires a reception signal related to the reflected light received by the light receiving element array 22 from the light receiving element array 22. The reception signal has intensity related to the light intensity of the reflected light received by each of the plurality of light receiving parts disposed on the light receiving face of the light receiving element array 22. The control unit 23 processes the reception signal under different conditions in the calibration period and the pulse measurement period.

In the calibration period, the control unit 23 acquires the reception signal from the light receiving element array 22 that has received the reflected light of the modulated light for calibration. The control unit 23 calculates the degree of influence for each of the plurality of light emitters 21 on each of the plurality of light receiving parts disposed on the light receiving face of the light receiving element array 22. The control unit 23 sets a normalization constant of each of the plurality of light emitters 21 for each of the plurality of light receiving parts based on the calculated degree of influence.

In the pulse measurement period, the control unit 23 acquires the reception signal from the light receiving element array 22 that has received the reflected light of the optical signal for pulse measurement. The control unit 23 acquires a reception signal from each of the plurality of light receiving parts disposed on the light receiving face of the light receiving element array 22. The control unit 23 optimizes the intensity of the acquired reception signal. The control unit 23 optimizes the intensity of the reception signal by multiplying the intensity of the reception signal acquired from each of the plurality of light receiving parts by a normalization constant set for each of the plurality of light receiving parts for each of the plurality of light emitters 21.

The control unit 23 outputs a normalized signal (also referred to as a pulse signal). The control unit 23 may output the pulse signal via a wire such as a cable or may output the pulse signal via wireless communication. For example, the control unit 23 is configured to output a pulse signal via a wireless communication function (not illustrated) conforming to a standard such as Bluetooth (registered trademark) or WiFi (registered trademark). The communication function of the control unit 23 may conform to a standard other than Bluetooth (registered trademark) or WiFi (registered trademark). The output destination and application of the pulse signal are not particularly limited.

The substrate 24 has a configuration similar to that of the substrate 14 of the first example embodiment. The substrate 24 is a bendable substrate. The substrate 24 has a bendable plate-like shape. The light emitter 21, the light receiving element array 22, and the control unit 23 mounted on the substrate 24 may be configured to be deformed or may be configured not to be deformed according to the deformation of the substrate 24.

The adhesive layer 27 has a configuration similar to that of the adhesive layer 17 of the first example embodiment. The adhesive layer 27 is formed in a peripheral portion of the measurement face of the substrate 24.

Figure 22:
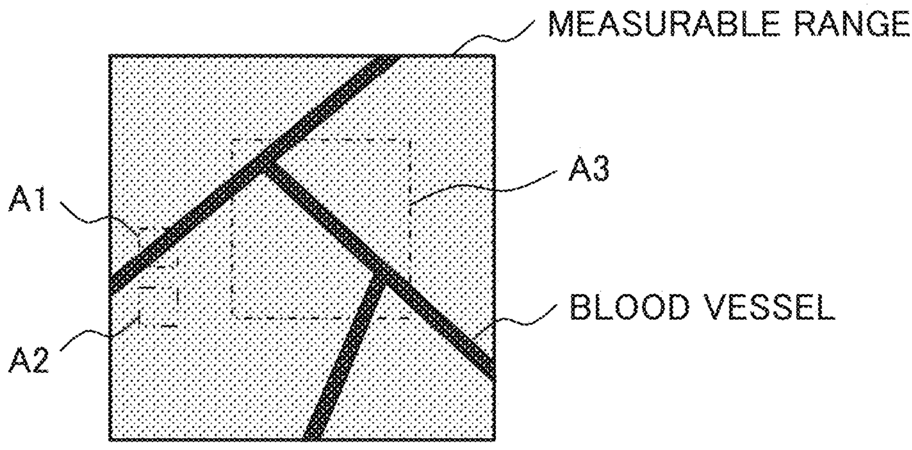
FIG. 22 is a conceptual diagram illustrating an example of an environment of a measurement range measured by the pulse measurement device according to the second example embodiment.

FIG. 22 is a conceptual diagram illustrating an example of an environment of skin application to which the pulse measurement device 20 is attached. The measurable range is a range facing the light receiving face of the light receiving element array 22. In the example of FIG. 22, the measurable range includes a plurality of blood vessels. For example, the measurable range includes a range A1 including a single blood vessel, a range A2 not including a blood vessel, and a range A3 including a plurality of blood vessels. For example, when the intensity of the pulse signal based on the reflected light received by the light receiving element array 22 at a certain timing is two-dimensionally mapped, the position of the blood vessel in the measurable range can be identified. For example, when images (frames) obtained by two-dimensionally mapping the intensity of the pulse signal based on the reflected light received by the light receiving element array 22 in a certain period are continuously connected in time series, a video in which the fluctuation of the pulse in the measurable range can be observed is obtained.

Figure 23:
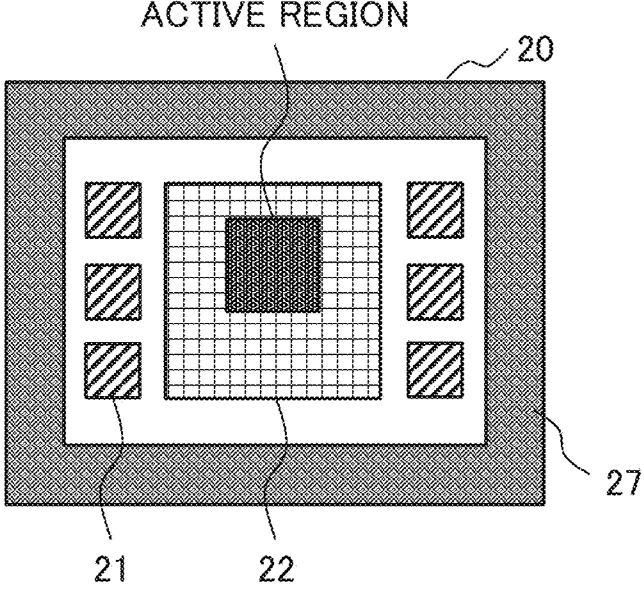
FIG. 23 is a conceptual diagram for describing an active region set in a light receiving element array of a pulse measurement device according to the second example embodiment.

FIG. 23 illustrates an example in which part of the light receiving face of the light receiving element array 22 is set to the active region where the pulse measurement is performed. The active region is a range related to the region to be measured set within the measurable range. The region to be measured is a range to be subjected to pulse measurement. For example, when the position of the blood vessel within the measurable range is identified in the calibration period, the range to be measured is set according to the position of the blood vessel to be measured. For example, when only a main blood vessel included in the measurable range is to be measured, the light receiving range at a position immediately above the blood vessel is set as the range to be measured. For example, when not a main blood vessel included in the measurable range but a capillary vessel or the like is to be measured, the light receiving range immediately above the capillary vessel or the like avoiding the position immediately above the main blood vessel is set as the range to be measured. In this way, when the range to be measured is set, the inspection can be performed focusing on the blood vessel and the pulsation to be measured, so that the usability is improved. When the range to be measured is set, signal process of an unnecessary range can be omitted, so that power consumption of the pulse measurement device 20 can be reduced. For example, when any one of the plurality of light emitters 21 is set to stop light emission according to the position of the range to be measured, power consumption related to light emission of the light emitter 21 can be reduced.

Figure 24:
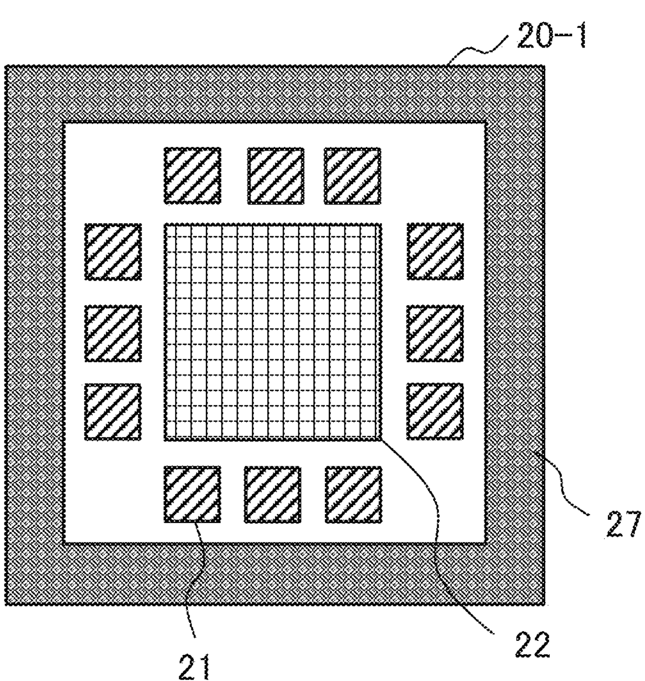
FIG. 24 is a conceptual diagram for describing a modification of the pulse measurement device according to the second example embodiment.

FIG. 24 is a modification of the pulse measurement device 20 of FIG. 19 (pulse measurement device 20-1). In the pulse measurement device 20-1, a plurality of light emitters 21 is disposed along four sides of the light receiving element array 22. In the pulse measurement device 20-1, the optical signal can be emitted not only from the two left and right directions of the light receiving element array 22 but also from the two upper and lower directions. Therefore, an optical signal can be emitted from more directions under the skin. For example, there is a possibility that the optical signal by the radiation of the optical signal from two directions of up and down reaches a blood vessel hidden at a position where the optical signal is not radiated in the radiation of the optical signal from two directions of right and left. For example, the plurality of light emitters 21 disposed around the light receiving element array 22 is operated for each disposed position (side). Then, by combining the pulse signals measured with respect to the respective positions (sides), the state of the blood vessel under the skin can be three-dimensionally grasped. For example, when the light emitter 21 that is optimal for the measurement of the blood vessel or the pulsation to be measured is selected and operated among the plurality of light emitters 21 disposed on the upper, lower, left, and right sides of the light receiving element array 22, the power consumption related to the light emission of the light emitter 21 can be reduced.

(Operation)

Next, an example of the operation of the pulse measurement device 20 according to the present example embodiment will be described with reference to the drawings. Hereinafter, an example of the operation of the pulse measurement device 20 will be described along a flowchart with the control unit 23 as an operation subject.

[Calibration]

Figure 25:
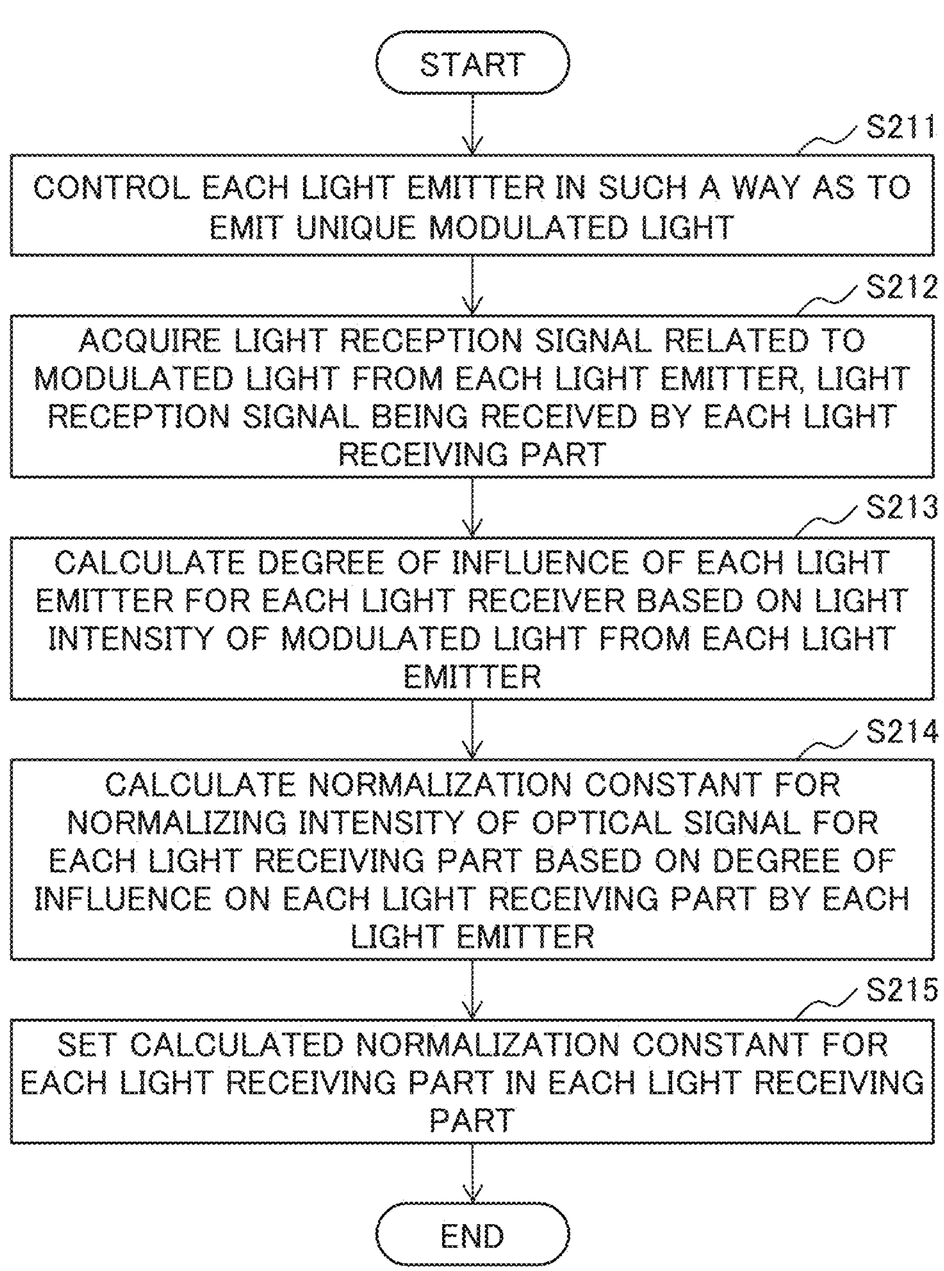
FIG. 25 is a flowchart for describing an example of calibration by the pulse measurement device according to the second example embodiment.

FIG. 25 is a flowchart for describing an example of the operation in the calibration period by the control unit 23 of the pulse measurement device 20. The flowchart of FIG. 25 is an example in which the plurality of light emitters 21 is operated simultaneously to perform calibration. The flowchart of FIG. 25 is related to the flowchart of FIG. 11 used in the first example embodiment. When calibration is performed by operating each of the plurality of light emitters 11 one by one, calibration may be performed in a procedure similar to the flowchart of FIG. 12 used in the first example embodiment.

In FIG. 25, first, the control unit 23 controls each of the plurality of light emitters 21 in such a way as to emit unique modulated light (step S211). In a case where calibration is performed by operating the plurality of light emitters 21 at the same time, the control unit 23 causes each of the plurality of light emitters 21 to emit unique modulated light having different frequencies.

The control unit 23 acquires a reception signal related to the modulated light from the plurality of light emitters 21, the reception signal being received by each of the plurality of light receiving parts disposed on the light receiving face of the plurality of light receiving element arrays 22 (step S212).

The control unit 23 calculates the degree of influence of the plurality of light emitters 21 for each light receiving part based on the light intensity of the modulated light from the plurality of light emitters 21 (step S213). The light intensity of the modulated light is reflected on the intensity of the reception signal related to the modulated light received by the plurality of light receiving parts of the light receiving element array 22.

The control unit 23 calculates a normalization constant for normalizing the light intensity of the optical signal for each of the light receiving parts based on the degree of influence of each of the plurality of light emitters 21 on each of the plurality of light receiving parts (step S214).

The control unit 23 sets the calculated normalization constant for each light receiving part in each of the plurality of light receiving parts (step S215). In the case of adjusting the optical output of the light emitter 21, the control unit 23 sets the calculated normalization constant for each light receiving part in each of the plurality of light receiving parts.

[Setting of Range to be Measured]

FIG. 26 illustrates an example in which the range to be measured is set in the measurable range of the light receiving element array 22 (related to the example of FIG. 23). Among the plurality of light receiving parts disposed on the light receiving face of the light receiving element array 22, the light receiving part inside the range (active region) related to the range to be measured is calibrated. The operation of the flowchart of FIG. 26 is executed prior to calibration of the light receiving part disposed inside the active region.

In FIG. 26, first, the control unit 23 controls the plurality of light emitters 21 in such a way to emit detection light for detecting a blood vessel in the measurable range (step S221). The plurality of light emitters 21 may be controlled to emit detection light having the same frequency, or may be controlled to emit detection light modulated at frequencies different from each other.

The control unit 23 acquires a reception signal related to the detection light from each of the plurality of light emitters 21, the reception signal being received by the plurality of light receiving parts disposed on the light receiving face of the light receiving element array 22 (step S222).

The control unit 23 identifies the position of the blood vessel in the measurable range based on the reception signal related to the detection light from the plurality of light emitters 21 (step S223). For example, the control unit 23 identifies the position of the blood vessel in the measurable range according to the intensity of the pulse signal obtained by the detection light. For example, the control unit 23 identifies the position of the blood vessel in the measurable range according to the magnitude relationship of the pulse signal obtained by the detection light. For example, the control unit 23 may output a pulse signal obtained by the detection light to a terminal device or the like (not illustrated) to urge an operator of the terminal device or the like to set the range to be measured.

The control unit 23 sets a range to be measured to be measured according to the identified position of the blood vessel (step S224). For example, the control unit 23 may set the range to be measured according to an instruction input by an operator who has checked a screen of a terminal device or the like. For example, the operator may set the range to be measured with respect to the two-dimensional image of the pulse signal displayed on the screen of the terminal device (not illustrated) through a pointing device or a touch panel. The region to be measured is not limited to a rectangle, and may be set to an any shape. For example, in a case where input through a touch panel is possible, the range to be measured may be set by tracing the panel with a finger in such a way as to surround the range to be measured.

The control unit 23 sets a normalization constant for the light receiving part in the range (active region) related to the set inside of the range to be measured (step S225). The normalization constant is set according to the procedure of the flowchart of FIG. 25. When the range to be measured is set according to the procedure of the flowchart of FIG. 26, the power consumption in the signal process of the reception signal can be reduced. For example, when the light emitter 21 that emits an optical signal is selected or the optical output of the light emitter 21 is set according to the set range to be measured, the power consumption of the light emitter 21 can be reduced.

[Pulse Measurement]

Figure 27:
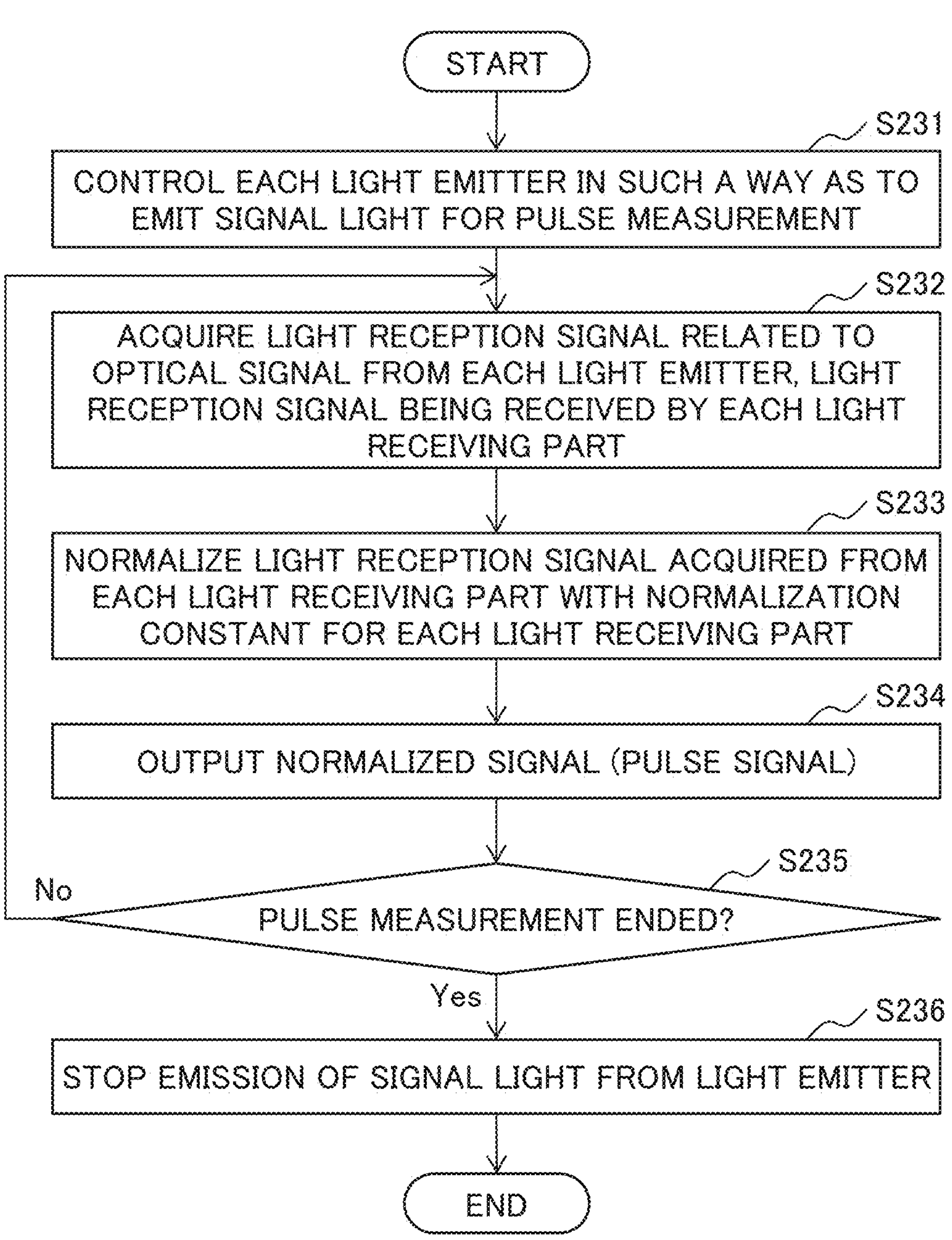
FIG. 27 is a flowchart for describing an example of pulse measurement by the pulse measurement device according to the second example embodiment.

FIG. 27 is a flowchart for describing an example of the operation in the pulse measurement period by the control unit 23 of the pulse measurement device 20. The flowchart of FIG. 27 relates to a pulse measurement period in a stage where calibration related to the light receiving element array 22 is completed.

In FIG. 27, first, the control unit 23 controls each of the plurality of light emitters 21 in such a way as to emit an optical signal for pulse measurement (step S231). In the case of adjusting the optical output of the light emitter 21, the control unit 23 adjusts the optical output of each of the plurality of light emitters 11 according to the normalization constant of each light receiving part.

Next, the control unit 23 acquires a reception signal related to the reflected light of the optical signal from each of the plurality of light emitters 21, the reception signal being received by each of the plurality of light receiving parts disposed on the light receiving face of the light receiving element array 22 (step S232).

Next, the control unit 23 optimizes the reception signal acquired from each of the plurality of light receiving parts with a normalization constant for each light receiving part (step S233).

Next, the control unit 23 outputs a normalized signal (pulse signal) (step S234). For example, the control unit 23 outputs a pulse signal to a terminal device, a portable terminal, an external system, a display device, or the like (not illustrated).

When ending the pulse measurement (Yes in step S235), the control unit 23 stops the emission of the optical signals from the plurality of light emitters 21 (step S236). When the pulse measurement is continued (No in step S235), the process returns to step S232. For example, the end/continuation of the pulse measurement is determined according to a preset schedule. For example, the end/continuation of the pulse measurement may be set at an any timing according to the input operation of the user.

As described above, the pulse measurement device of the present example embodiment includes the plurality of light emitters, the light receiving element array, and the control unit. The plurality of light emitters is disposed on a measurement face of a substrate attached to the skin of the subject to be subjected to pulse measurement. The plurality of light emitters emits light toward the skin of the subject. The light receiving element array is disposed on the measurement face of the substrate. The light receiving element array includes a plurality of light receiving parts that receives reflected light of light emitted from the plurality of light emitters. The light receiving element array has a light receiving face in which a plurality of light receiving parts is disposed in a two-dimensional array. The control unit causes the plurality of light emitters to emit light. The control unit receives a reception signal related to reflected light of light received by the light receiver from the light receiving element array. The control unit optimizes the intensity of the reception signal using the normalization constant set for each of the plurality of light emitters. The control unit outputs the reception signal whose intensity is optimized using the normalization constant as a pulse signal.

In the pulse measurement device of the present example embodiment, the reflected light of the light emitted from the plurality of light emitters is received by the light receiving element array. The pulse measurement device of the present example embodiment normalizes the intensity of the reception signal related to the reflected light received by each of the plurality of light receiving parts disposed on the light receiving face of the light receiving element array for each light emitter. Therefore, according to the present example embodiment, since the intensity of the reception signal according to the reflected light of the light emitted from the plurality of light emitters can be uniformly normalized in each of the plurality of light receiving parts, the pulse of the subject can be measured more accurately. According to the present example embodiment, the state of the blood vessel within the measurable range can be two-dimensionally visualized.

In an aspect of the present example embodiment, the control unit causes the plurality of light emitters to emit detection light for detecting the position of the blood vessel included in the measurable range of the light receiving element array. The control unit sets the range to be measured in the measurable range based on the reception signal related to the reflected light of the detection light received by the light receiving element array. The control unit sets a normalization constant for the light receiving part in the range related to the set range to be measured. According to the present aspect, the range to be measured is set according to the position of the blood vessel included in the measurable range of the light receiving element array, and the inspection can be performed focusing on the blood vessel and the pulsation to be measured, so that the usability is improved. According to the present aspect, since signal process in an unnecessary range can be omitted, power consumption of the pulse measurement device can be reduced.

According to the method of the present example embodiment, the position of the blood vessel in the measurable range can be two-dimensionally accurately grasped. The two-dimensional information of the blood vessel obtained by the method of the present example embodiment can be applied to biological authentication such as vein authentication. According to the method of the present example embodiment, the pulse in the measurable range can be two-dimensionally accurately grasped. The two-dimensional information of the pulse obtained by the method of the present example embodiment can also be applied to diagnosis of skin cancer and diagnosis of the state of sores/burns. For example, when the light emitters are disposed around the entire circumference of the light receiving element array, the blood vessel in the measurable range can be three-dimensionally grasped.

Third Example Embodiment

Next, a biological information estimation device according to a third example embodiment will be described with reference to the drawings. The biological information estimation device according to the present example embodiment estimates biological information about a subject based on pulse signals output from the pulse measurement devices according to the first and second example embodiments.

(Configuration)

Figure 28:
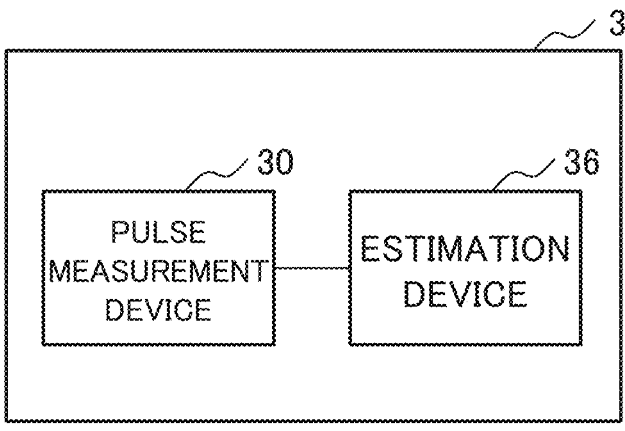
FIG. 28 is a block diagram illustrating an example of a configuration of a biological information estimation device according to a third example embodiment.

FIG. 28 is a block diagram illustrating an example of a configuration of a biological information estimation device 3 according to the present example embodiment. The biological information estimation device 3 includes a pulse measurement device 30 and an estimation device 36. The pulse measurement device 30 is the pulse measurement device of each of the first and second example embodiments. Detailed description of the pulse measurement device 30 will be omitted.

The estimation device 36 acquires the pulse signal output from the pulse measurement device 30. The estimation device 36 estimates biological information of the subject according to the acquired pulse signal. The biological information of the subject includes a pulse, a physical condition, an emotion, and the like.

For example, the estimation device 36 estimates the pulse of the subject based on the pulse signal. For example, the estimation device 36 estimates the pulse according to the interval of the maximum value/minimum value appearing in the time-series data of the pulse signal. For example, the estimation device 36 estimates the pulse according to the expression cycle of the feature amount extracted from the time-series data of the pulse signal. The estimation device 36 outputs information about the pulse such as the estimated pulse interval and the intensity of the pulse signal.

For example, the estimation device 36 estimates the physical condition of the subject based on the pulse signal. For example, the estimation device 36 estimates the physical condition of the subject based on the time-series data of the pulse signal. When the subject is at rest, the intensity of the pulse signal decreases and the pulse interval increases. When the subject is exercising, the intensity of the pulse signal increases and the pulse interval decreases. When the subject has an irregular heartbeat, the pulse rhythm is irregular or the pulse is interrupted. The physical condition of the subject also affects the baseline of the time-series data of the pulse signal. When the subject's physical condition is stable, the baseline variation is small. On the other hand, in a case where the physical condition of the subject is unstable, the fluctuation of the baseline increases. For example, the baseline shows a rising tendency or a falling tendency depending on the physical condition of the subject. In a case where the subject suffers from some disease, a characteristic peculiar to the disease may appear in the pulse signal. When an estimation model that is trained on a feature appearing in a pulse signal due to a disease in advance is used, it is possible to estimate a disease that the subject suffers according to the pulse signal of the subject. The estimation device 36 outputs information about the estimated physical condition of the subject.

For example, the physical condition such as stress, fatigue, and sleepiness held by the subject also affects the pulse signal. The estimation device 36 extracts a feature amount according to a physical condition such as stress, fatigue, and drowsiness from the pulse time-series data. For example, the estimation device 36 extracts feature amounts such as an average value, a standard deviation, a coefficient of variation, a root mean square, and a frequency component of the pulse time-series data from the pulse time-series data. The estimation device 36 estimates the physical condition of the subject according to the extracted feature amount. The estimation device 36 outputs information about the estimated physical condition of the subject, recommendation information according to the estimated physical condition, and the like.

For example, the estimation device 36 estimates the emotion of the subject based on the pulse signal. The emotion of the subject can be estimated by the intensity or fluctuation of the pulse. For example, the estimation device 36 estimates the degree of emotions such as pleasure, anger, sorrow, and delight according to the fluctuation of the pulse time-series data. For example, the estimation device 36 may estimate the emotion of the subject according to the variation in the baseline of the time-series data related to the pulse. For example, as the "anger" of the subject gradually increases, an increasing tendency appears in the baseline according to an increase in the degree of excitement (awakeness level) of the subject. For example, as the "sorrow" of the subject gradually increases, a downward tendency appears in the baseline according to the decrease in the degree of excitement (awakeness level of the subject.

Figure 29:
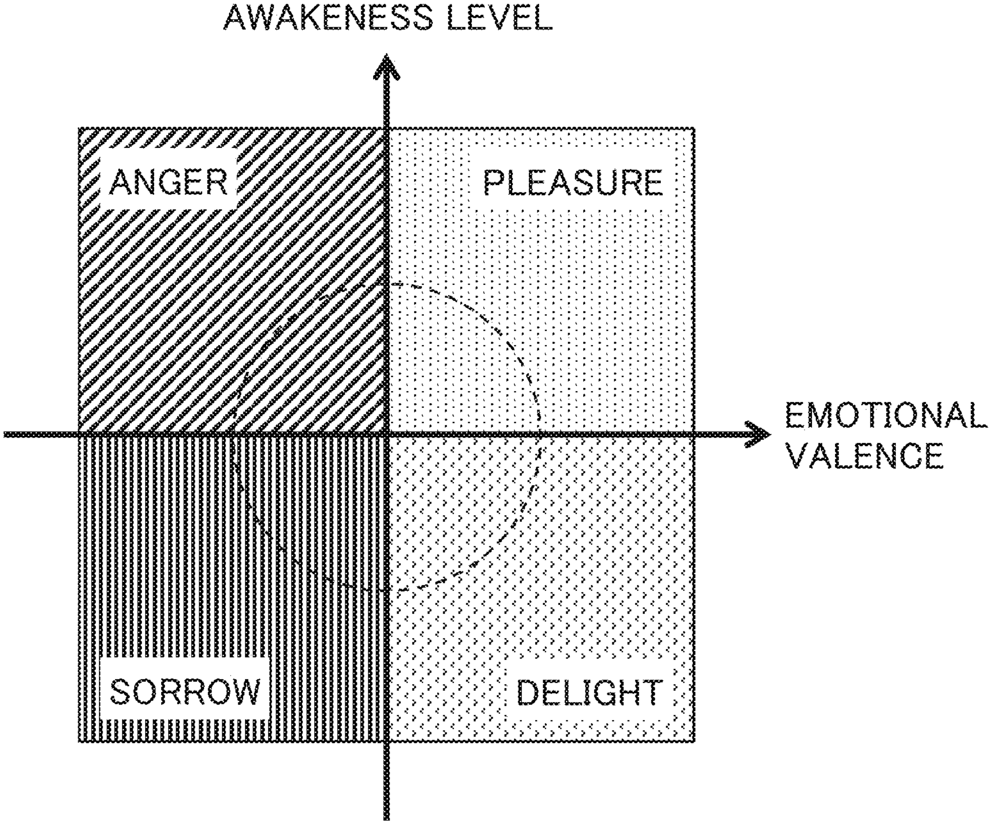
FIG. 29 is a conceptual diagram for describing an emotion state estimated by the biological information estimation device according to the third example embodiment.

FIG. 29 is a conceptual diagram for describing an example of estimating an emotion based on a pulse signal. In the example of FIG. 29, the emotion is estimated according to the relationship between the emotional valence (horizontal axis) and the awakeness level (vertical axis). The emotional valence (horizontal axis) quantifies emotional comfort. The emotional valence (horizontal axis) indicates a more comfortable state toward the right and a more uncomfortable state toward the left. The awakeness level (vertical axis) quantifies emotional arousal. The awakeness level (vertical axis) indicates a more excited state toward the top and a calmer state toward the bottom. In the example of FIG. 29, emotions of delight, anger, sorrow, and delight are associated with each quadrant defined by the emotional valence (horizontal axis) and the awakeness level (vertical axis). "Pleasure" is associated with the first quadrant. The greater the emotional valence and the greater the awakeness level, the greater the degree of "pleasure". The second quadrant is associated with "anger". The lower the emotional valence and the higher the awakeness level, the higher the degree of "anger". "Sorrow" is associated with the third quadrant. The lower the emotional valence and the lower the awakeness level, the higher the degree of "sorrow". "Delight" is associated with the fourth quadrant. The higher the emotional valence and the lower the awakeness level, the higher the degree of "delight". The association of emotions with respect to the graph of FIG. 29 is an example, and does not limit the criteria for emotion estimation by the biological information estimation device 3 of the present example embodiment. For example, the emotion of the subject is not classified into four emotion states such as delight, anger, sorrow, and delight, but may be classified into more detailed emotion states. The emotion of the subject may be classified not only by the two-dimensional coordinate system as illustrated in FIG. 29 but also by an any emotion state classification method.

The heart rate fluctuates under the influence of activity related to the autonomic nerve such as sympathetic nerve and parasympathetic nerve. Similarly, the pulse rate fluctuates under the influence of activity related to the autonomic nerve such as sympathetic nerve and parasympathetic nerve. For example, a low frequency component or a high frequency component can be extracted by frequency analysis of time-series data of the pulse rate. The influence of the sympathetic nerve and the parasympathetic nerve is reflected in the low frequency component. The influence of the parasympathetic nerve is reflected in the high frequency component. Therefore, for example, the activity state of the autonomic nerve function can be estimated according to the ratio between the high frequency component and the low frequency component.

Sympathetic nerves tend to be active when the subject is excited. When the sympathetic nerve of the subject is active, pulsation is fast. That is, the greater the pulse rate, the greater the awakeness level. Parasympathetic nerves tend to be active when the subject is relaxed. When the subject relaxes, the pulsation is slow. That is, the smaller the pulse rate, the smaller the awakeness level. In this manner, the estimation device 36 can measure the awakeness level in accordance with the pulse rate. For example, the emotional valence can be evaluated according to the variation in the pulse interval. The more pleasant the emotion state, the more stable the emotion and the smaller the variation in the pulse interval. That is, the smaller the variation in the pulse interval, the larger the emotional valence. On the other hand, the more unpleasant the emotion state, the more unstable the emotion, and the larger the variation in the pulse interval. That is, the greater the variation in the pulse interval, the greater the emotional valence. In this manner, the estimation device 36 can measure the emotional valence according to the pulse interval. However, the method of measuring the awakeness level and the emotional valence is not limited to the method and the standard described above as long as the pulse signal output from the pulse measurement device 30 is used.

The estimation device 36 estimates the awakeness level and the emotional valence based on the time-series data of the pulse signal. The estimation device 36 estimates the emotion according to the measured coordinates of the awakeness level and the emotional valence in the coordinate system of the graph of FIG. 29. When the coordinates of the awakeness level and the emotional valence measured for a certain subject are in the first quadrant, the estimation device 36 estimates that the emotion state of the subject is "pleasure". When the coordinates of the awakeness level and the emotional valence measured for a subject are in the second quadrant, the estimation device 36 estimates that the emotion state of the subject is "anger". When the coordinates of the awakeness level and the emotional valence measured for a certain subject are in the third quadrant, the estimation device 36 estimates that the emotion state of the subject is "sorrow". When the coordinates of the awakeness level and the emotional valence measured for a certain subject are in the fourth quadrant, the estimation device 36 estimates that the emotion state of the subject is "delight". For example, in a case where the emotional valence and the awakeness level do not exceed the threshold value, the estimation device 36 determines that the emotion state of the subject is a normal state. For example, if the coordinates of the emotional valence and the awakeness level are inside a circle of a broken line shown at the center of the coordinate system in FIG. 29, the estimation device 36 determines that the emotion state of the subject is a normal state. The threshold value for determining that the emotion state of the subject is a normal state can be set to any value. For example, such a threshold value may be different for each emotion of delight, anger, sorrow, and delight.

Figure 30:
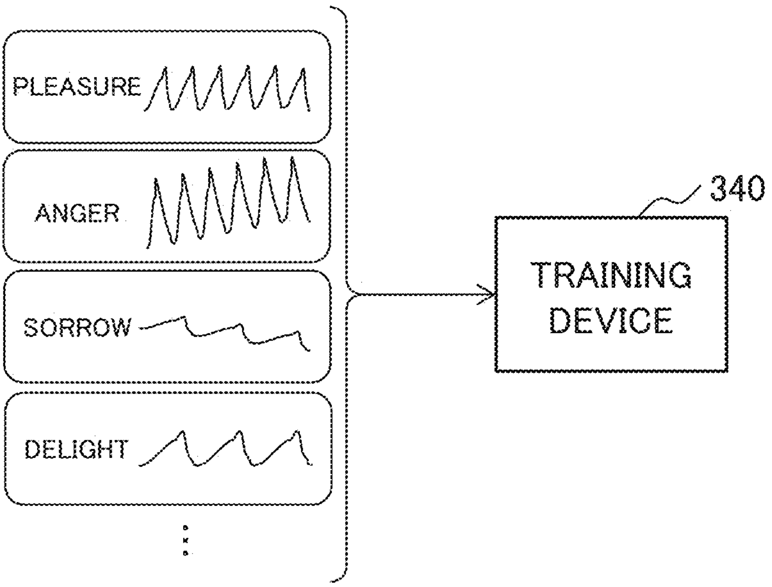
FIG. 30 is a conceptual diagram for describing an example of generation of an estimation model used by the biological information estimation device according to the third example embodiment.

The estimation device 36 may be configured to estimate an emotion using a machine training method. FIG. 30 is a conceptual diagram illustrating an example of a training device 340 with which a data set of a feature amount (explanatory variable) extracted from a pulse signal and an emotion (response variable) is trained as teacher data. The teacher data is data in which the label of the emotion state at that time is given to the feature amount extracted from the pulse signal measured for the subject in any of the emotion states of delight, anger, sorrow, and delight. The teacher data may be data in which a label of the emotion state at that time is given to a pulse signal measured for a subject in any emotion state of delight, anger, sorrow, and delight. The training device 340 generates an estimation model 360 by supervised learning using teacher data. For example, the estimation model 360 is generated in advance by the training device 340 trained with teacher data related to a plurality of subjects. The estimation model 360 outputs the estimation result of the emotion of the subject according to the input of the feature amount extracted from the pulse signal. A specific method of machine training is not particularly limited.

Figure 31:
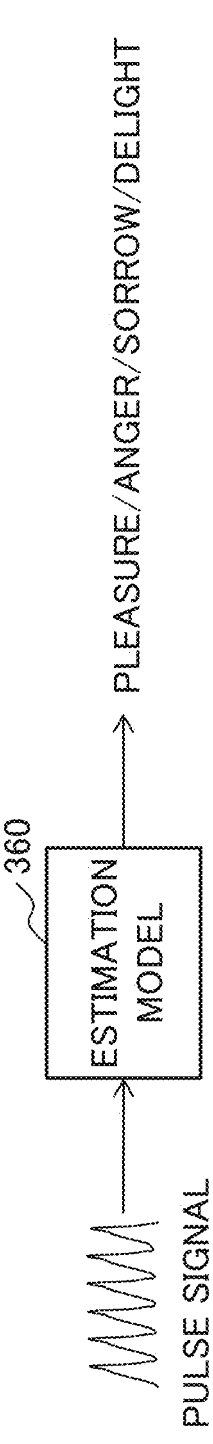
FIG. 31 is a conceptual diagram for describing an example of estimation of an emotion state using an estimation model by the biological information estimation device according to the third example embodiment.

FIG. 31 is a conceptual diagram for describing an example of emotion estimation by the estimation model 360. In the example of FIG. 31, the estimation result of any emotion of delight, anger, sorrow, and delight is output from the estimation model 360 according to the input of the pulse signal of the subject. For example, the information about the estimation result of the emotion output from the estimation model 360 is displayed on a screen of a terminal device or the like (not illustrated).

Figures 32, 33:
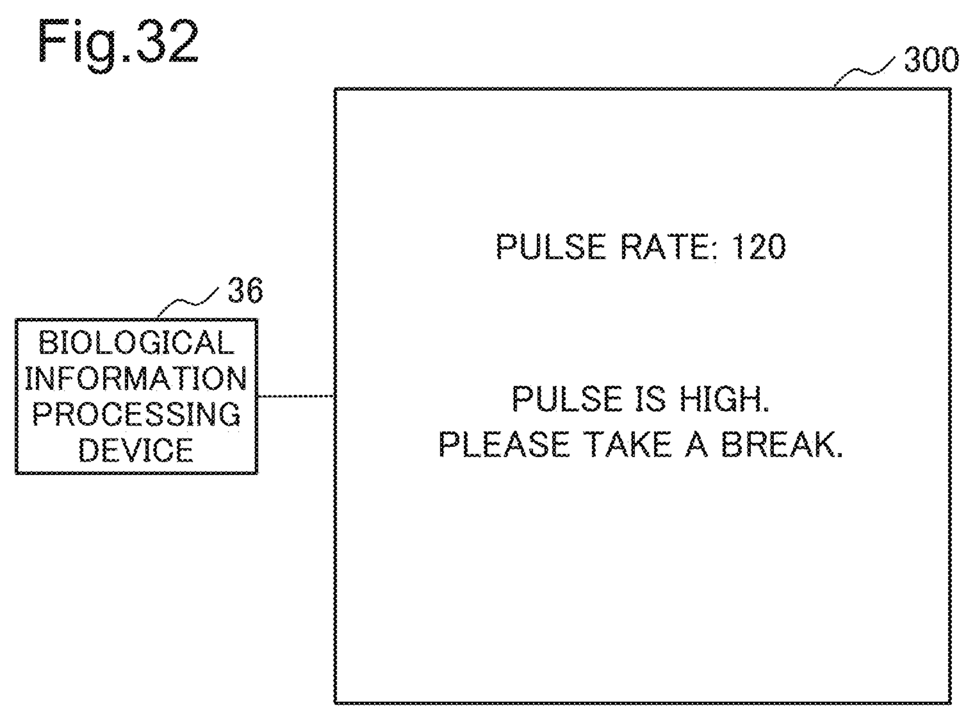
FIG. 32 is a conceptual diagram illustrating an example in which information related to a pulse rate estimated by the biological information estimation device according to the third example embodiment is displayed on a screen.
FIG. 33 is a conceptual diagram illustrating an example of displaying information according to an emotion state estimated by the biological information estimation device according to the third example embodiment on a screen.

FIG. 32 illustrates an example in which the pulse rate measured according to the pulse signal output from the pulse measurement device 30 is displayed on the screen of a terminal device 300. In the example of FIG. 32, the recommendation information according to the pulse rate is also displayed on the screen of the terminal device 300. The subject who visually recognizes the pulse rate displayed on the screen can confirm his/her pulse rate. The subject who has visually recognized the recommendation information displayed on the screen can improve his/her physical condition by acting in accordance with the recommendation information.

FIG. 33 illustrates an example in which the emotion state of the subject according to the pulse signal output from the pulse measurement device 30 is displayed on the screen of the terminal device 300. In the example of FIG. 33, the recommendation information according to the emotion state of the subject is also displayed on the screen of the terminal device 300. In the example of FIG. 33, the emotion state of the subject is "angry". For example, a face letter or an icon indicating the emotion state of the subject may be displayed on the screen of the terminal device 300. The subject who has visually recognized the emotion state displayed on the screen can confirm his/her emotion state. The subject who has visually recognized the recommendation information displayed on the screen can bring his/her emotion state close to a normal state by paying attention to the recommendation information. However, the recommendation information displayed on the screen does not necessarily cause the subject to change the emotion state as expected. For example, the estimated emotion state of the subject may be transmitted to a terminal device (not illustrated) owned by a family member or an acquaintance of the subject. With this configuration, there is a possibility that the emotion state of the subject can be brought closer to the normal state according to the behavior of another person in a close relationship with the subject instead of the inorganic information displayed on the screen.

In the example of FIG. 33, a flower image is also displayed on the screen of the terminal device 300 in order to soften the emotion state of the subject toward a normal state. The image to be displayed on the screen may be any image as long as there is a possibility of softening the emotion state of the subject. What is displayed on the screen of the terminal device 300 may be not only an image but also a video. Music that softens the emotion state of the subject may be played from a speaker (not illustrated) of the terminal device 300. For example, in a case where the emotion state of the subject is "sorrow", content such as an image, a video, and music that comfort the subject may be provided to the subject. For example, in a case where the emotion state of the subject is "pleasure" or "delight", content that maintains the emotion state may be provided to the subject. The content provided to the subject is preferably set for each emotion of the subject. For example, a function of inputting whether the provided information is adapted to the subject's emotion may be added. When it is configured to learn the user's reaction to information provided according to the estimated emotion and feed back to the emotion estimation thereafter, the emotion of the subject can be estimated more accurately.

For example, the pulse measurement device 30 may be worn by a driver of an automobile to provide recommendation information according to the emotion state of the driver. For example, a safe driving environment can be provided by recommending the driver to take a break or notifying the driver of a predicted arrival time to the next parking area according to the estimation result of the emotion state of the driver of the automobile. For example, in a case where the emotion state of the driver of the automobile is "angry" or "sorrow", music or a message for soothing or comforting the driver's emotion may be played. For example, in a case where the emotion state of the driver of the automobile is "delight", music or a message prompting the driver to have some tension may be played. For example, in a case where the emotion state of the driver of the automobile is "pleasure", music or a message that is likely to maintain the emotion state may be played. For example, recommendation information according to a driver's emotion state and driving time may be provided. For example, in a case where driving time is long and a tendency of "anger" appears in emotion, recommendation information such as "go to next parking area and rise up and exercise" may be provided to the driver. For example, in a case where driving time is long and a tendency of "sorrow" appears in emotions, recommendation information such as "go to next parking area and sleep" may be provided to the driver.

For example, the attention distraction level of the driver may be estimated based on the emotion state of the driver. The attention distraction level tends to be high in an extreme emotion state. Therefore, for example, in a case where the awakeness level or the emotional valence is extremely large or extremely small, the attention distraction level is estimated to be high. A threshold value related to the attention distraction level may be set for the awakeness level or the emotional valence, and the attention distraction level of the driver may be estimated according to the relationship with the threshold value. For example, in a case where the attention distraction level exceeds a threshold value, a notification sound for calling attention may be emitted.

For example, the pulse measurement device 30 may be worn by the user who lives a daily life, and recommendation information according to the emotion state of the subject may be provided. For example, in a case where the emotion state of the user is "angry" or "sorrow", recommendation information recommending exercise such as walking or running may be provided in order to distract the user. For example, in a case where the user's emotion state is "angry" or "sorrow", music or information that makes it easy to shift the user's emotion state to "delight" or "pleasure" may be provided. For example, in a case where the user's emotion state is "delight" or "pleasure", music or information that can increase the emotion state may be provided. For example, in a case where the emotion state of the user is "delight" or "pleasure", obstructive information may not be provided in such a way that the environment at that time is maintained.

As described above, the biological information estimation device according to the present example embodiment includes a plurality of light emitters, a light receiver, a control unit, and an estimation device. The plurality of light emitters is disposed on a measurement face of a substrate attached to the skin of the subject to be subjected to pulse measurement. The plurality of light emitters emits light toward the skin of the subject. The light receiver is disposed on the measurement face of the substrate. The light receiver includes a plurality of light receiving parts that receives reflected light of light emitted from the plurality of light emitters. The control unit causes the plurality of light emitters to emit light. The control unit receives a reception signal related to reflected light of light received by the light receiver from the light receiver. The control unit optimizes the intensity of the reception signal using the normalization constant set for each of the plurality of light emitters. The control unit outputs the reception signal whose intensity is optimized using the normalization constant as a pulse signal. The estimation device acquires the pulse signal of the subject measured by the pulse measurement device. The estimation device estimates biological information of the subject based on the acquired pulse signal.

The biological information estimation device according to the present example embodiment estimates the emotion state of the subject as biological information based on a pulse signal output from a pulse measurement device including a plurality of light receiving parts normalized for each of a plurality of light emitters. Therefore, according to the present example embodiment, the biological information of the subject can be accurately estimated.

In an aspect of the present example embodiment, the estimation device estimates the pulse rate of the subject using the pulse signal of the subject. The estimation device outputs information related to the estimated pulse rate. According to the present aspect, the pulse rate of the subject can be monitored by outputting information related to the pulse rate of the subject. For example, when the pulse rate is displayed on a screen of a terminal device or the like, the pulse rate of the subject can be visually monitored.

In an aspect of the present example embodiment, the estimation device estimates the emotion state of the subject using the pulse signal of the subject. The estimation device outputs information related to the estimated emotion state. According to the present aspect, the emotion state of the subject can be monitored by outputting information related to the emotion state of the subject. For example, by displaying the emotion state on a screen of a terminal device or the like, the emotion state of the subject can be visually monitored.

Fourth Example Embodiment

Figure 34:
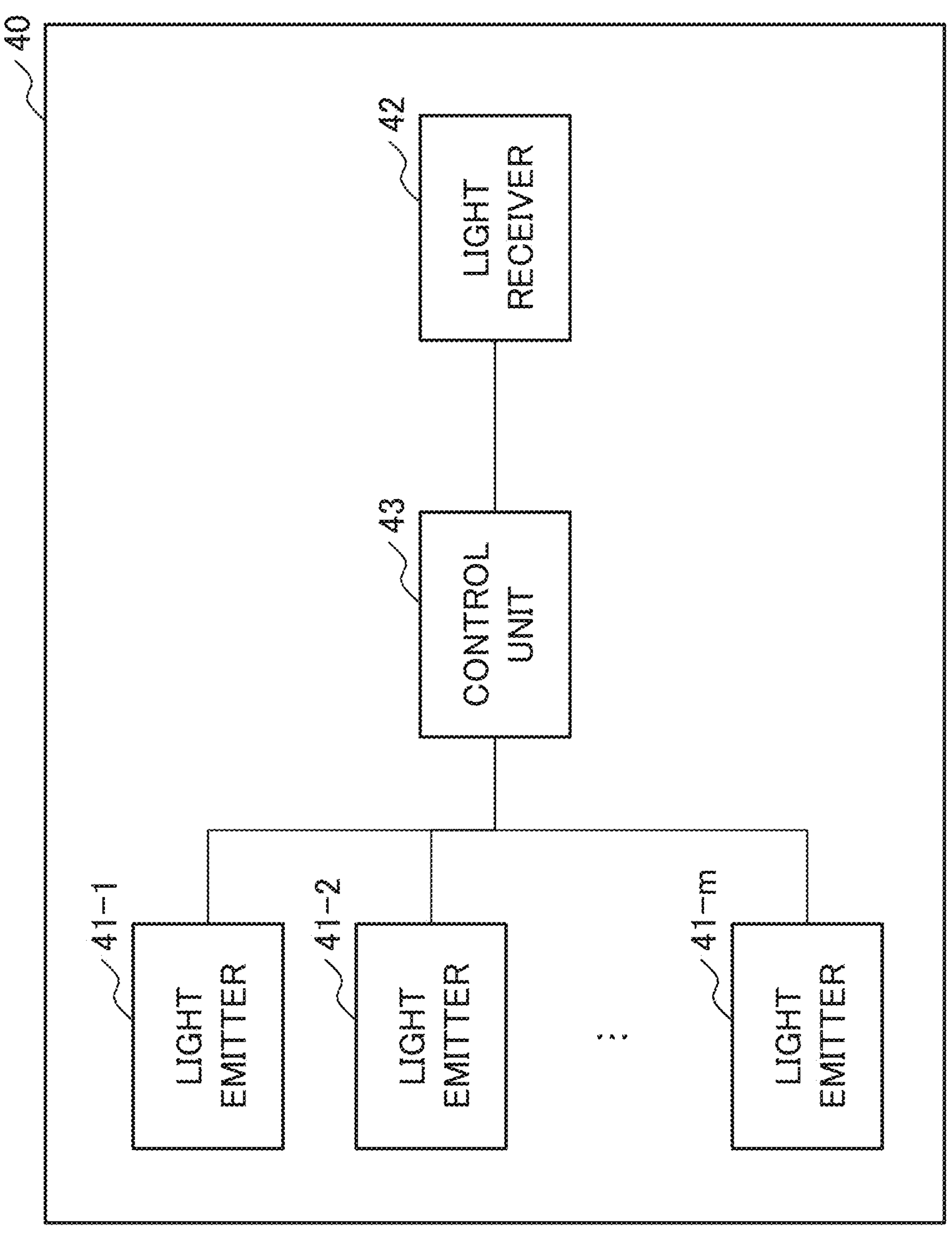
FIG. 34 is a block diagram illustrating an example of a configuration of a pulse measurement device according to a fourth example embodiment.

Next, a pulse measurement device according to the fourth example embodiment will be described with reference to the drawings. The pulse measurement device of the present example embodiment has a configuration in which of the first to third pulse measurement devices are simplified. FIG. 34 is a block diagram illustrating an example of a configuration of a pulse measurement device 40 according to the present example embodiment. The pulse measurement device 40 includes a plurality of light emitters 41-1 to m, a light receiver 42, and a control unit 43 (m is a natural number equal to or more than 2).

The plurality of light emitters 41-1 to m is disposed on a measurement face of a substrate (not illustrated) attached to the skin of the subject to be subjected to pulse measurement. The plurality of light emitters 41-1 to m emits light toward the skin of the subject. The light receiver 42 is disposed on the measurement face of the substrate. The light receiver 42 includes a plurality of light receiving parts that receives reflected light of light emitted from the plurality of light emitters 41-1 to m. The control unit 43 causes the plurality of light emitters 41-1 to m to emit light. The control unit 43 receives a reception signal related to the reflected light of the light received by the light receiver 42 from the light receiver 42. The control unit 43 optimizes the intensity of the reception signal using the normalization constant set for each of the plurality of light emitters 41-1 to m. The control unit 43 outputs the reception signal whose intensity is optimized using the normalization constant as a pulse signal.

The pulse measurement device of the present example embodiment normalizes the intensity of the reception signal related to the reflected light reflected/scattered inside the human body of the light emitted from the plurality of light emitters toward the human body for each light emitter. Therefore, according to the present example embodiment, by uniformly normalizing the intensity of the reception signal according to the reflected light of the light emitted from the plurality of light emitters, the influence of the heartbeat and the body motion artifact is removed. Therefore, according to the present example embodiment, the pulse of the subject can be accurately measured.

(Hardware)

Regarding a hardware configuration that executes control and processing according to each example embodiment of the present disclosure, an information processing device 90 in FIG. 35 will be described as an example. The information processing device 90 in FIG. 35 is a configuration example for performing control and a process of each example embodiment, and does not limit the scope of the present disclosure.

Figure 35:
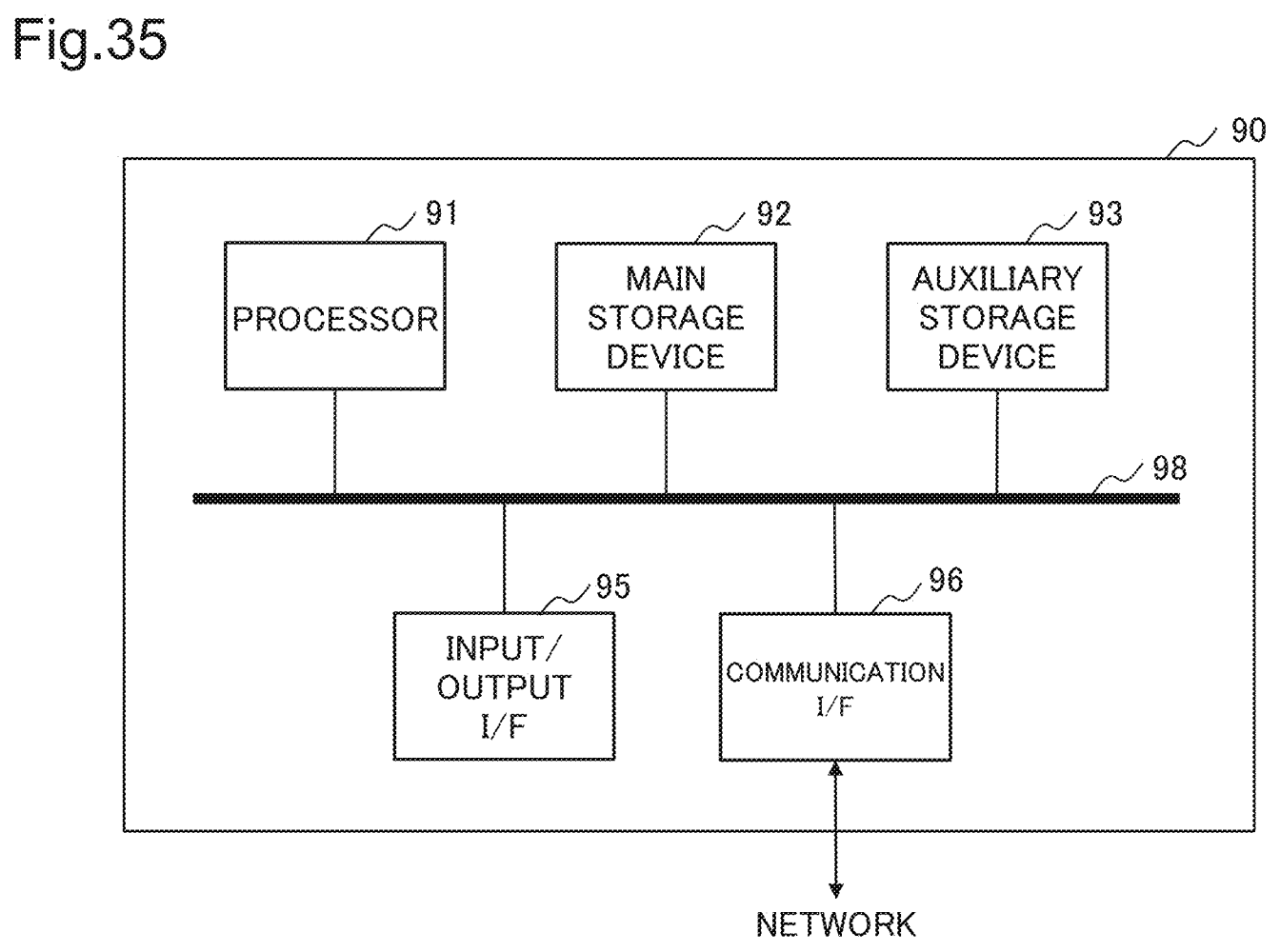

As illustrated in FIG. 35, the information processing device 90 includes a processor 91, a main storage device 92, an auxiliary storage device 93, an input/output interface 95, and a communication interface 96. In FIG. 35, the interface is abbreviated as an interface (I/F). The processor 91, the main storage device 92, the auxiliary storage device 93, the input/output interface 95, and the communication interface 96 are data-communicably connected to each other via a bus 98. The processor 91, the main storage device 92, the auxiliary storage device 93, and the input/output interface 95 are connected to a network such as the Internet or an intranet via the communication interface 96.

The processor 91 develops the program stored in the auxiliary storage device 93 or the like in the main storage device 92. The processor 91 executes the program developed in the main storage device 92. In the present example embodiment, a software program installed in the information processing device 90 may be used. The processor 91 executes control and processing according to the present example embodiment.

The main storage device 92 has an area in which a program is developed. A program stored in the auxiliary storage device 93 or the like is developed in the main storage device 92 by the processor 91. The main storage device 92 is achieved by, for example, a volatile memory such as a dynamic random access memory (DRAM). A nonvolatile memory such as a magnetoresistive random access memory (MRAM) may be configured and added as the main storage device 92.

The auxiliary storage device 93 stores various pieces of data such as programs. The auxiliary storage device 93 is achieved by a local disk such as a hard disk or a flash memory. Various pieces of data may be stored in the main storage device 92, and the auxiliary storage device 93 may be omitted.

The input/output interface 95 is an interface that connects the information processing device 90 with a peripheral device based on a standard or a specification. The communication interface 96 is an interface that connects to an external system or a device through a network such as the Internet or an intranet in accordance with a standard or a specification. The input/output interface 95 and the communication interface 96 may be shared as an interface connected to an external device.

An input device such as a keyboard, a mouse, or a touch panel may be connected to the information processing device 90 as necessary. These input devices are used to input of information and settings. In a case where the touch panel is used as the input device, the display screen of the display device may also serve as the interface of the input device. Data communication between the processor 91 and the input device may be mediated by the input/output interface 95.

The information processing device 90 may be provided with a display device that displays information. In a case where a display device is provided, the information processing device 90 preferably includes a display control device (not illustrated) that controls display of the display device. The display device may be connected to the information processing device 90 via the input/output interface 95.

The information processing device 90 may be provided with a drive device. The drive device mediates reading of data and a program from the recording medium, writing of a processing result of the information processing device 90 to the recording medium, and the like between the processor 91 and the recording medium (program recording medium). The drive device may be connected to the information processing device 90 via the input/output interface 95.

The above is an example of a hardware configuration for enabling control and processing according to each example embodiment of the present invention. The hardware configuration of FIG. 35 is an example of a hardware configuration for executing control and processing according to each example embodiment, and does not limit the scope of the present invention. A program for causing a computer to execute control and processing according to each example embodiment is also included in the scope of the present invention. A program recording medium in which the program according to each example embodiment is recorded is also included in the scope of the present invention. The recording medium can be achieved by, for example, an optical recording medium such as a compact disc (CD) or a digital versatile disc (DVD). The recording medium may be achieved by a semiconductor recording medium such as a Universal Serial Bus (USB) memory or a secure digital (SD) card. The recording medium may be achieved by a magnetic recording medium such as a flexible disk, or another recording medium. In a case where the program executed by the processor is recorded in the recording medium, the recording medium corresponds to a program recording medium.

The components of each example embodiment may be combined in any manner. The components of each example embodiment may be achieved by software or may be achieved by a circuit.

While the present invention is described with reference to example embodiments thereof, the present invention is not limited to these example embodiments. Various modifications that can be understood by those of ordinary skill in the art can be made to the configuration and details of the present invention within the scope of the present invention.

Some or all of the above example embodiments may be described as the following Supplementary Notes, but are not limited to the following.

(Supplementary Note 1)

A pulse measurement device including a plurality of light emitters that is disposed on a measurement face of a substrate to be attached to a skin of a subject to be subjected to pulse measurement and emits light toward the skin of the subject, a light receiver that is disposed on the measurement face of the substrate and includes a plurality of light receiving parts that receives reflected light of the light emitted from the plurality of light emitters, and a control unit that causes the plurality of light emitters to emit the light, receives, from the light receiver, a reception signal related to the reflected light of the light received by each of the light receivers, optimizes intensity of the reception signal using a normalization constant set for each of the plurality of light emitters, and outputs the reception signal having intensity optimized using the normalization constants as a pulse signal.

(Supplementary Note 2)

The pulse measurement device according to Supplementary Note 1, wherein the control unit optimizes an optical output of each of the plurality of light emitters according to the normalization constant set for each of the plurality of light emitters.

(Supplementary Note 3)

The pulse measurement device according to Supplementary Note 1 or 2, wherein the control unit, during a calibration period, emits modulated light modulated at a specific frequency from each of the plurality of light emitters, calculates a degree of influence of each of the plurality of light emitters on each of the plurality of light receiving parts according to received light intensity of reflected light of the modulated light for each of the plurality of light emitters in each of the plurality of light receiving parts included in the light receiver, and sets the normalization constant by which intensity of the reception signal according to the reflected light of the modulated light emitted from each of the plurality of light emitters is uniform in each of the plurality of light receiving parts according to the degree of influence calculated for each of the plurality of light emitters on each of the plurality of light receiving parts.

(Supplementary Note 4)

The pulse measurement device according to Supplementary Note 1 or 2, wherein the control unit, during a pulse measurement period, emits an optical signal from each of the plurality of light emitters, and optimizes intensity of the reception signal by multiplying the reception signal related to the reflected light of the optical signal of each of the plurality of light emitters, the reception signal being acquired from each of the plurality of light receiving parts, by the normalization constant of each of the plurality of light emitters, the normalization constant being set in each of the plurality of light receiving parts.

(Supplementary Note 5)

The pulse measurement device according to any one of Supplementary Notes 1 to 4, wherein the light receiver includes a light receiving element array in which the plurality of light receiving parts is disposed in a two-dimensional array.

(Supplementary Note 6)

The pulse measurement device according to Supplementary Note 5, wherein the control unit causes the plurality of light emitters to emit detection light for detecting a position of a blood vessel included in a measurable range of the light receiving element array, sets a range to be measured in the measurable range based on the reception signal related to the reflected light of the detection light received by the light receiving element array, and sets the normalization constant for the light receiving part in a range related to the set range to be measured.

(Supplementary Note 7)

A biological information estimation device including the pulse measurement device according to any one of Supplementary Notes 1 to 6, and an estimation device that acquires a pulse signal of a subject measured by the pulse measurement device and estimates biological information of the subject based on the acquired pulse signal.

(Supplementary Note 8)

The biological information estimation device according to Supplementary Note 7, wherein the estimation device estimates a pulse rate of the subject using the pulse signal of the subject, and outputs information related to the estimated pulse rate.

(Supplementary Note 9)

The biological information estimation device according to Supplementary Note 7, wherein the estimation device estimates an emotion state of the subject using the pulse signal of the subject, and outputs information according to the estimated emotion state.

(Supplementary Note 10)

A control method of controlling a plurality of light emitters that emits light toward a skin of a subject to be subjected to pulse measurement and a light receiver including a plurality of light receiving parts that receives reflected light of the light emitted from the plurality of light emitters, the control method including a control unit causing the plurality of light emitters to emit the light, receiving, from the light receiver, a reception signal related to the reflected light of the light received by each of the light receivers, optimizing intensity of the reception signal using a normalization constant set for each of the plurality of light emitters, and outputting the reception signal having intensity optimized using the normalization constants as a pulse signal.

(Supplementary Note 11)

A non-transitory recording medium storing a program for controlling a plurality of light emitters that emits light toward a skin of a subject to be subjected to pulse measurement and a light receiver including a plurality of light receiving parts that receives reflected light of the light emitted from the plurality of light emitters, the program causing a computer to execute the steps of causing the plurality of light emitters to emit the light, receiving, from the light receiver, a reception signal related to the reflected light of the light received by each of the light receivers, optimizing intensity of the reception signal using a normalization constant set for each of the plurality of light emitters, and outputting the reception signal having intensity optimized using the normalization constants as a pulse signal.

REFERENCE SIGNS LIST

3 biological information estimation device
10, 20, 30, 40 pulse measurement device
11, 21, 41 light emitter
12, 42 light receiver
13, 23, 43 control unit
14, 24 substrate
17, 27 adhesive layer
22 light receiving element array
36 estimation device
100, 300 terminal device
131, 231 light emission control unit
132, 232 signal acquisition unit
133, 233 normalization constant setting unit
134, 234 storage unit
135, 235 optimization unit
136, 236 output unit

What is claimed is:

1. A pulse measurement device comprising:

a plurality of light emitters that is disposed on a measurement face of a substrate to be attached to a skin of a subject to be subjected to pulse measurement and emits light toward the skin of the subject;

at least one light receiver that is disposed on the measurement face of the substrate and includes a plurality of light receiving parts that receives reflected light of the light emitted from the plurality of light emitters; and a controller comprising a first memory storing instructions; and a first processor connected to the first memory and configured to execute the instructions to cause the plurality of light emitters to emit the light, receive, from the at least one light receiver, a reception signal related to the reflected light of the light received by each of the at least one light receivers, optimize intensity of the reception signal using a normalization constant determined during a calibration period by emitting modulated light modulated at a specific frequency from each of the plurality of light emitters, calculating a degree of influence of each of the plurality of light emitters on each of the plurality of light receiving parts according to received light intensity of reflected light of the modulated light, set the normalization constant by which the intensity of the reception signal is uniform in each of the plurality of light receiving parts, the normalization constant being individually set for each of the plurality of light emitters for each of the plurality of light receiving parts, and output the reception signal having the intensity optimized using the normalization constants as a pulse signal.

2. The pulse measurement device according to claim 1, wherein the first processor is further configured to execute the instructions to optimize an optical output of each of the plurality of light emitters according to the normalization constant set for each of the plurality of light emitters.

3. The pulse measurement device according to claim 1, wherein the first processor is further configured to execute the instructions to, during a pulse measurement period, emit an optical signal from each of the plurality of light emitters, and optimize the intensity of the reception signal by multiplying the reception signal related to the reflected light of the optical signal of each of the plurality of light emitters, the reception signal being acquired from each of the plurality of light receiving parts, by the normalization constant of each of the plurality of light emitters, the normalization constant being set in each of the plurality of light receiving parts.

4. The pulse measurement device according to claim 1, wherein the light receiver includes a light receiving element array in which the plurality of light receiving parts is disposed in a two-dimensional array.

5. The pulse measurement device according to claim 4, wherein the first processor is further configured to execute the instructions to;

cause the plurality of light emitters to emit detection light for detecting a position of a blood vessel included in a measurable range of the light receiving element array, set a range to be measured in the measurable range based on the reception signal related to the reflected light of the detection light received by the light receiving element array, and set the normalization constant for each of the plurality of light receiving parts in a range related to the set range to be measured.

6. A biological information estimation device comprising: the pulse measurement device according to claim 1; and an estimation device comprising:

a second memory storing instructions; and a second processor connected to the second memory and configured to execute the instructions to:

acquire a pulse signal of a subject measured by the pulse measurement device, and estimate biological information of the subject based on the acquired pulse signal.

7. The biological information estimation device according to claim 6, wherein the second processor is further configured to execute the instructions to:

estimate a pulse rate of the subject using the pulse signal of the subject, and output information related to the estimated pulse rate.

8. The biological information estimation device according to claim 6, wherein the second processor is further configured to execute the instructions to;

estimate an emotion state of the subject using the pulse signal of the subject, and output information according to the estimated emotion state.

9. The biological information estimation device according to claim 8, wherein the second processor is further configured to execute the instructions to;

estimate the emotion state of the subject by using a machine training method, and wherein the information according to the estimated emotion state is for providing recommended information to enable a decision making by the subject to bring the emotion state of the subject closer to a normal state.

10. A pulse measurement method using a plurality of light emitters that emits light toward a skin of a subject to be subjected to pulse measurement and at least one light receiver including a plurality of light receiving parts that receives reflected light of the light emitted from the plurality of light emitters, the pulse measurement method causing controller to execute:

causing the plurality of light emitters to emit the light;

receiving, from the at least one light receiver, a reception signal related to the reflected light of the light received by each of the at least one light receivers;

optimizing intensity of the reception signal using a normalization constant determined during a calibration period by emitting modulated light modulated at a specific frequency from each of the plurality of light emitters, calculating a degree of influence of each of the plurality of light emitters on each of the plurality of light receiving parts according to received light intensity of reflected light of the modulated light;

setting the normalization constant by which the intensity of the reception signal is uniform in each of the plurality of light receiving parts, the normalization constant being individually set for each of the plurality of light emitters for each of the plurality of light receiving parts; and outputting the reception signal having the intensity optimized using the normalization constants as a pulse signal.

11. A non-transitory recording medium storing a program for controlling a plurality of light emitters that emits light toward a skin of a subject to be subjected to pulse measurement and at least one light receiver including a plurality of light receiving parts that receives reflected light of the light emitted from the plurality of light emitters, the program causing a computer to execute the steps of:

causing the plurality of light emitters to emit the light;

receiving, from the at least one light receiver, a reception signal related to the reflected light of the light received by each of the at least one light receivers;

optimizing intensity of the reception signal using a normalization constant determined during a calibration period by emitting modulated light modulated at a specific frequency from each of the plurality of light emitters, calculating a degree of influence of each of the plurality of light emitters on each of the plurality of light receiving parts according to received light intensity of reflected light of the modulated light;

setting the normalization constant by which the intensity of the reception signal is uniform in each of the plurality of light receiving parts, the normalization constant being individually set for each of the plurality of light emitters for each of the plurality of light receiving parts; and outputting the reception signal having the intensity optimized using the normalization constants as a pulse signal.

* * * * *